(12) United States Patent
Tanaka

(10) Patent No.: US 8,821,380 B2
(45) Date of Patent: Sep. 2, 2014

(54) ANTENNA APPARATUS, ANTENNA, ANTENNA HOLDER, AND BODY-INSERTABLE APPARATUS SYSTEM

(71) Applicant: Olympus Medical Systems Corp., Tokyo (JP)

(72) Inventor: Shinsuke Tanaka, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/690,759

(22) Filed: Nov. 30, 2012

(65) Prior Publication Data
US 2013/0178702 A1 Jul. 11, 2013

Related U.S. Application Data

(63) Continuation of application No. PCT/JP2012/063755, filed on May 29, 2012.

(30) Foreign Application Priority Data

May 30, 2011 (JP) ................................. 2011-120248

(51) Int. Cl.
| | | |
|---|---|---|
| A61B 1/04 | (2006.01) | |
| A61B 5/06 | (2006.01) | |
| A61B 5/07 | (2006.01) | |
| A61B 5/00 | (2006.01) | |
| H01Q 1/00 | (2006.01) | |
| A61B 1/00 | (2006.01) | |

(52) U.S. Cl.
CPC ............... *A61B 1/00009* (2013.01); *A61B 1/04* (2013.01); *A61B 5/061* (2013.01); *A61B 5/07* (2013.01); *A61B 5/6801* (2013.01); *A61B 1/041* (2013.01); *H01Q 1/00* (2013.01); *A61B 1/00016* (2013.01)
USPC ............................ 600/109; 600/102; 600/121

(58) Field of Classification Search
CPC ............. A61B 1/00131; A61B 1/0014; A61B 1/00147; A61B 5/6831
USPC .......................................................... 600/102
See application file for complete search history.

(56) References Cited

U.S. PATENT DOCUMENTS 3,604,012 A * 9/1971 Lindley .......................... 343/768
3,683,933 A * 8/1972 Mansfield ....................... 607/36

(Continued)

FOREIGN PATENT DOCUMENTS

| CN | 101366622 A | 2/2009 |
|---|---|---|
| CN | 101742962 A | 6/2010 |

(Continued)

OTHER PUBLICATIONS

English language translation of International Search Report PCT/JP2012/063755 dated Sep. 4, 2012.

*Primary Examiner* — Anhtuan T Nguyen
*Assistant Examiner* — Jae Woo
(74) *Attorney, Agent, or Firm* — Scully, Scott, Murphy & Presser, P.C.

(57) ABSTRACT

An antenna apparatus is configured to acquire information from a body-insertable apparatus that is configured to be inserted into a subject to move inside the subject. The antenna apparatus includes an antenna that includes one sheet on which plural receiving antennas are fixed and in which a first positioning hole is formed; and an antenna holder that includes a container portion which is configured to hold the antenna at a predetermined position and in a predetermined orientation and in which second positioning hole is formed at a position corresponding to the first positioning hole when the antenna is held. The antenna holder is configured to be attached to a predetermined position of the subject using the first and second positioning holes as an index when the antenna is held in the antenna holder.

5 Claims, 18 Drawing Sheets

(56) References Cited

U.S. PATENT DOCUMENTS

| | | | |
|---|---|---|---|
| 4,540,001 A * | 9/1985 | Ewing | 600/519 |
| 4,563,668 A * | 1/1986 | Martino | 340/908.1 |
| 5,451,972 A * | 9/1995 | Franklin | 343/840 |
| 6,198,394 B1 * | 3/2001 | Jacobsen et al. | 340/573.1 |
| 7,076,284 B2 | 7/2006 | Segawa et al. | 600/424 |
| 7,083,579 B2 | 8/2006 | Yokoi et al. | 600/593 |
| 7,151,503 B2 | 12/2006 | Noro et al. | 343/872 |
| 7,160,258 B2 * | 1/2007 | Imran et al. | 600/593 |
| 7,295,877 B2 | 11/2007 | Govari | 607/60 |
| 7,456,801 B2 * | 11/2008 | Kubokawa et al. | 343/872 |
| 7,492,320 B2 | 2/2009 | Kimoto | 343/718 |
| 7,558,620 B2 | 7/2009 | Ishibashi | 600/476 |
| 7,604,591 B2 * | 10/2009 | Uchiyama et al. | 600/130 |
| 7,801,586 B2 | 9/2010 | Muratayev et al. | 600/407 |
| 7,804,461 B2 * | 9/2010 | Kubokawa et al. | 343/872 |
| 7,804,462 B2 * | 9/2010 | Kubokawa et al. | 343/872 |
| 7,866,322 B2 * | 1/2011 | Iddan | 128/899 |
| 8,259,013 B2 | 9/2012 | Jang et al. | 343/700 MS |
| 8,372,001 B2 * | 2/2013 | Akagi | 600/109 |
| 8,446,332 B2 | 5/2013 | Homan | 343/810 |
| 8,457,755 B2 | 6/2013 | Snitting | 607/60 |
| 2002/0173718 A1 * | 11/2002 | Frisch et al. | 600/424 |
| 2004/0077937 A1 * | 4/2004 | Yarden | 600/386 |
| 2005/0043634 A1 * | 2/2005 | Yokoi et al. | 600/476 |
| 2005/0148816 A1 | 7/2005 | Glukhovsky et al. | |
| 2005/0194012 A1 * | 9/2005 | Ito et al. | 128/899 |
| 2006/0122494 A1 * | 6/2006 | Bouchoucha | 600/424 |
| 2006/0183993 A1 | 8/2006 | Horn | |
| 2007/0188401 A1 | 8/2007 | Kubokawa et al. | |
| 2007/0252892 A1 | 11/2007 | Fujita et al. | |
| 2007/0293781 A1 * | 12/2007 | Sims et al. | 600/534 |
| 2008/0068453 A1 * | 3/2008 | Mori et al. | 348/65 |
| 2008/0108872 A1 * | 5/2008 | Glukhovsky et al. | 600/117 |
| 2008/0272978 A1 | 11/2008 | Kubokawa et al. | |
| 2008/0291112 A1 | 11/2008 | Kubokawa et al. | |
| 2009/0054731 A1 * | 2/2009 | Shigemori | 600/118 |
| 2009/0118576 A1 * | 5/2009 | Akagi et al. | 600/109 |
| 2009/0131759 A1 * | 5/2009 | Sims et al. | 600/301 |
| 2009/0247896 A1 * | 10/2009 | Kanai et al. | 600/547 |
| 2009/0281381 A1 * | 11/2009 | Takenaka et al. | 600/109 |
| 2010/0130885 A1 * | 5/2010 | Hamaguchi et al. | 600/547 |
| 2010/0198100 A1 * | 8/2010 | Oku et al. | 600/547 |
| 2010/0268025 A1 * | 10/2010 | Belson | 600/109 |
| 2012/0157769 A1 * | 6/2012 | Zhu et al. | 600/109 |
| 2013/0123575 A1 * | 5/2013 | Homan | 600/103 |
| 2013/0225981 A1 * | 8/2013 | Hasegawa | 600/424 |
| 2013/0237809 A1 * | 9/2013 | Hasegawa | 600/424 |
| 2013/0253269 A1 * | 9/2013 | Hasegawa et al. | 600/109 |

FOREIGN PATENT DOCUMENTS

| | | |
|---|---|---|
| JP | 11-42214 | 2/1999 |
| JP | 2006-6489 | 1/2006 |
| JP | 2006-26163 | 2/2006 |
| JP | 2006-187611 | 7/2006 |
| JP | 2006-271987 | 10/2006 |
| JP | 2008-295883 | 12/2008 |
| WO | WO 2007/043271 | 4/2007 |
| WO | WO 2009/011180 | 1/2009 |
| WO | 2010/044389 A1 | 4/2010 |

* cited by examiner

ANTENNA APPARATUS, ANTENNA, ANTENNA HOLDER, AND BODY-INSERTABLE APPARATUS SYSTEM

CROSS-REFERENCE TO RELATED APPLICATIONS

This application is a continuation of PCT international application Ser. No. PCT/JP2012/063755 filed on May 29, 2012 which designates the United States based upon and claims the benefit of priority from Japanese Patent Application No. 2011-120248, filed on May 30, 2011, the entire contents of which are incorporated herein by reference.

BACKGROUND OF THE INVENTION

1. Field of the Invention

The present invention relates to an antenna apparatus that acquires information from a body-insertable apparatus that is inserted into a subject and moves inside the subject, an antenna, an antenna holder that holds the antenna, and a body-insertable apparatus system.

2. Description of the Related Art

In the related art, endoscopes have been widely used as a medical observation apparatus that is inserted into a subject to observe the inside of a body cavity. Moreover, in recent years, a swallowable endoscope (capsule endoscope) in which an imaging device and a communication device that wirelessly transmits image data captured by the imaging device are included in a capsule-shaped casing has been developed. The capsule endoscope has a function of moving inside an organ such as, for example, the esophagus, the stomach, or the small intestine according to a peristaltic motion of the organ until the capsule endoscope is naturally egested from the subject after being swallowed from the mouth of the subject in order to observe the inside of the body cavity.

The image data captured inside the body cavity by the capsule endoscope while moving inside the body cavity is sequentially transmitted to the outside of the body via wireless communication and is stored in a memory provided inside or outside a receiving device that is outside the body, or is displayed on a display provided in the receiving device as an image. A doctor or a nurse can import the image data stored in the memory to an information processing device via a cradle to which the receiving device is inserted and perform a diagnosis based on the image displayed on the display of the information processing device or the image that is received by the receiving device and displayed on the display.

When a wireless signal is received from a capsule endoscope, in general, in a receiving device, plural receiving antennas are distributed outside a subject, one receiving antenna having the strongest received strength is selected, and a wireless signal is received by the selected receiving antenna. As an example of such a receiving device, a receiving device that switches plural receiving antennas disposed outside a subject and estimates the position of a capsule endoscope which is a transmission source of a wireless signal based on the received field strengths of the respective receiving antennas is known. Specifically, a configuration in which plural compact antennas are attached to the belly of a subject and a moving state of a capsule endoscope is detected using a difference in the received strengths of the wireless signals of the respective antennas is proposed (for example, see Japanese Patent Application Laid-open No. 2006-26163). Moreover, a configuration in which plural antennas are fixed to a belt-shaped member and is wound around the belly of a subject so as to easily attach the plural antennas to the subject is also proposed (for example, see Japanese Patent Application Laid-open No. 2006-271987).

SUMMARY OF THE INVENTION

An antenna apparatus according to one aspect of the present invention is configured to acquire information from a body-insertable apparatus that is configured to be inserted into a subject to move inside the subject. The antenna apparatus includes: an antenna that includes one sheet on which plural receiving antennas are fixed and in which a first positioning hole is formed; and an antenna holder that includes a container portion which is configured to hold the antenna at a predetermined position and in a predetermined orientation and in which a second positioning hole is formed at a position corresponding to the first positioning hole when the antenna is held, the antenna holder being configured to be attached to a predetermined position of the subject using the first and second positioning holes as an index when the antenna is held. The antenna further includes a cable which extends from the sheet and in which wires connected to the respective receiving antennas are bundled. The sheet has an upper side and a bottom side that are parallel to an extension direction of the cable. A base end portion of the cable is disposed at a position that is deviated from an intermediate line of the upper and bottom sides of the sheet that are parallel to the extension direction of the cable.

An antenna according to another aspect of the present invention acquires information from a body-insertable apparatus configured to be inserted into a subject to move inside the subject. The antenna includes: one sheet on which plural receiving antennas are fixed; and a cable which extends from one side of the sheet and in which wires connected to the respective receiving antennas are bundled. A positioning hole is formed in the sheet. A base end portion of the cable is disposed at a position that is deviated from a line that passes through a center of the sheet and is parallel to an extension direction of the cable.

An antenna holder according to still another aspect of the present invention is configured to hold an antenna in which plural receiving antennas that acquire information from a body-insertable apparatus that is inserted into a subject and moves inside the subject are fixed on one sheet in which a first positioning hole is formed. The antenna holder includes a container portion which is configured to hold the antenna and in which a second positioning hole corresponding to the first positioning hole of the antenna is formed. The container portion has such a pouch shape that the antenna can be inserted and that has an opening that can be open and closed. A base end portion of a cable that extends from the antenna is positioned at an end portion of the opening when the antenna is held in the container portion to align the first positioning hole with the second positioning hole.

An antenna holder according to still another aspect of the present invention is configured to hold an antenna in which plural receiving antennas that acquire information from a body-insertable apparatus that is inserted into a subject and moves inside the subject are fixed on one polygonal sheet. The antenna holder includes: a container portion that has such a pouch shape that the antenna can be inserted and that has an opening that can be open and closed; a belt that is attached to the container portion to fix the container portion to the subject; a first rubber band that is formed on an outer surface of the container portion and is stretchable in an extension direction of the belt; and a second rubber band that is formed on the outer surface of the container portion and is stretchable in a direction crossing the extension direction of the belt.

A body-insertable apparatus system according to still another aspect of the present invention is inserted into a subject to acquire internal information of the subject. The body-insertable apparatus system includes: a body-insertable apparatus configured to be inserted into the subject to acquire an in-vivo image of the subject and wirelessly transmit image data to the outside while moving inside the subject; an antenna that includes one sheet on which plural receiving antennas that receive the image data transmitted wirelessly from the body-insertable apparatus are fixed and in which a first positioning hole is formed; and an antenna holder that includes a container portion which is configured to hold the antenna at a predetermined position and in a predetermined orientation and in which a second positioning hole is formed at a position corresponding to the first positioning hole when the antenna is held, the antenna holder being configured to be attached to a predetermined position of the subject using the first and second positioning holes as an index when the antenna is held; a receiving device that stores the image data received by the antenna and received signal strengths of the plural receiving antennas when the image data is received; and an information processing device to which the image data stored in the receiving device is transmitted and which displays the in-vivo image of the subject on a display unit. The antenna further includes a cable which extends from the sheet and in which wires connected to the respective receiving antennas are bundled. The sheet has an upper side and a bottom side that are parallel to an extension direction of the cable. A base end portion of the cable is disposed at a position that is deviated from an intermediate line of the upper and bottom sides of the sheet that are parallel to the extension direction of the cable. The information processing device includes a position information estimating unit configured to estimate position information of the body-insertable apparatus when the image data is received, based on the respective received signal strengths of the plural receiving antennas included in the image data.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
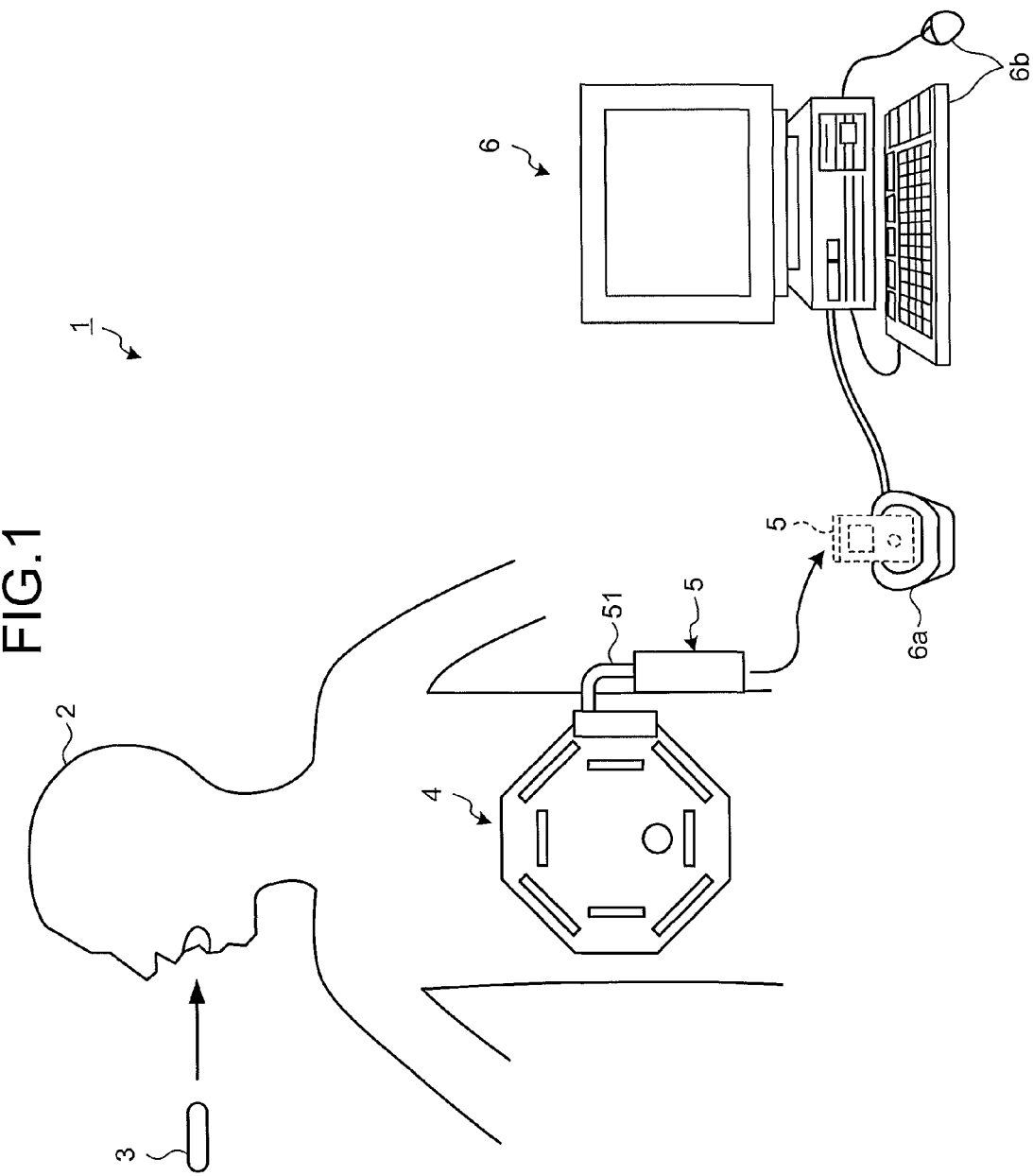
FIG. 1 is a schematic view illustrating an overall configuration of a body-insertable apparatus system according to a first embodiment.

Hereinafter, an antenna apparatus used in a position information estimation system that estimates the position of a capsule endoscope, an antenna, and an antenna holder for accommodating an antenna, which are embodiments of the present invention, will be described with reference to the drawings. The present invention is not limited to these embodiments. Moreover, in the respective drawings, the same portions are denoted by the same reference numerals. The drawings are illustrated schematically, and thus, it should be noted that the relation and ratio between the dimensions of each portion may be different from an actual case. The relation and ratio of dimensions may also be different in the respective drawings.

First Embodiment

Figure 2:
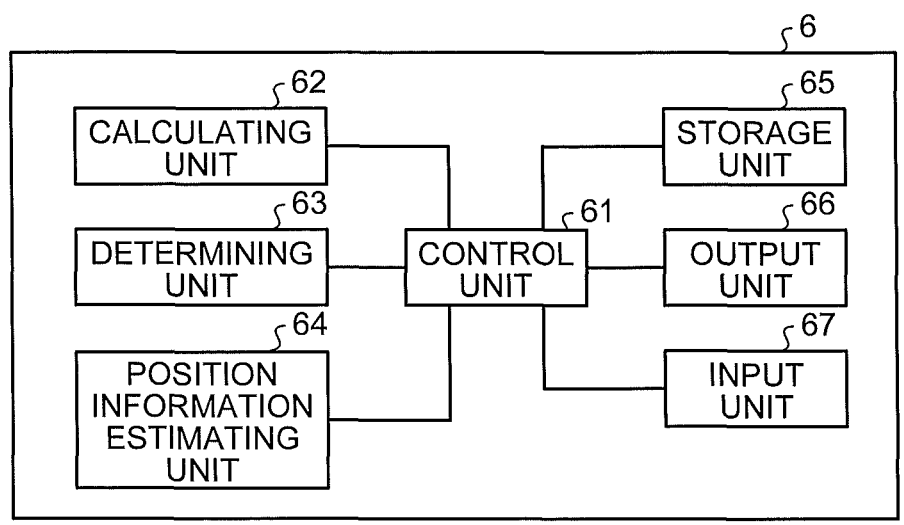
FIG. 2 is a block diagram illustrating a configuration of an information processing device of the body-insertable apparatus system according to the first embodiment.

First, a system that inserts a capsule endoscope into a subject, which is a position information estimation system according to a first embodiment of the present invention, will be described in detail with reference to the drawings. FIG. 1 is a schematic view illustrating an overall configuration of a body-insertable apparatus system according to the first embodiment of the present invention. FIG. 2 is a block diagram illustrating a configuration of an information processing device of the body-insertable apparatus system according to the first embodiment.

As illustrated in FIG. 1, a body-insertable apparatus system 1 includes a capsule endoscope 3 serving as a body-insertable apparatus that is inserted into a subject 2 so as to move inside the subject 2 to capture an in-vivo image, an acquisition antenna 4 that receives a wireless signal transmitted from the capsule endoscope 3 that is inserted into the subject 2, a receiving device 5 that performs a predetermined process on the wireless signal input from the acquisition antenna 4 and stores the processed wireless signal, and an information processing device 6 that processes and/or displays an image corresponding to the in-vivo image data of the subject 2 captured by the capsule endoscope 3. The acquisition antenna 4 and the receiving device 5 form a receiving unit.

The capsule endoscope 3 has a capturing function of capturing the in-vivo image of the subject 2 and a wireless communication function of transmitting image data obtained by capturing the in-vivo image of the subject 2 to the receiving device 5. Moreover, a circular coil antenna or a circular loop antenna is disposed in the capsule endoscope 3. The capsule endoscope 3 passes through the esophagus of the subject 2 by being swallowed into the subject 2 and moves along the body cavity according to a peristaltic motion of the lumen of the digestive tract. The capsule endoscope 3 sequentially captures the internal images of the body cavity of the subject 2 at a very small time interval (for example, at an interval of 0.5 seconds) while moving inside the body cavity to generate in-vivo image data of the subject 2 and sequentially transmits the in-vivo image data to the receiving device 5. In this case, the capsule endoscope 3 generates a transmission signal that includes image data and received field strength detection data that includes position information (beacon) or the like for making it easy to detect a received field strength and wirelessly transmits a wireless signal obtained by modulating the generated transmission signal to the receiving device 5.

The acquisition antenna 4 periodically receives the wireless signal from the capsule endoscope 3 and outputs the wireless signal to the receiving device 5 via an antenna cable 51. The acquisition antenna 4 is attached to the subject 2 by being fixed using a belt described later when an examination is conducted.

The receiving device 5 acquires the in-vivo image data of the subject 2 based on the wireless signal wirelessly transmitted from the capsule endoscope 3 via the acquisition antenna 4. The receiving device 5 stores position information and time information or the like that indicates a time in a memory in correlation with the received image data. During the period when an image is captured by the capsule endoscope 3, the receiving device 5 is carried on the subject 2 until the capsule endoscope 3 is egested from the subject 2 after being inserted through the mouth of the subject 2 and moving inside the digestive tract, for example. After the examination of the capsule endoscope 3 ends, the receiving device 5 is separated from the subject 2 and connected to the information processing device 6 in order to transmit information such as the image data received from the capsule endoscope 3.

The information processing device 6 is configured using a workstation or a personal computer that includes a display unit such as a liquid crystal display. The information processing device 6 displays an image corresponding to the in-vivo image data of the subject 2 acquired via the receiving device 5. The information processing device 6 includes a cradle 6a that reads image data from the memory of the receiving device 5 and an operation input device 6b such as a keyboard or a mouse.

Moreover, as illustrated in FIG. 2, the information processing device 6 includes a control unit 61 that performs control of the entire information processing device 6, a calculating unit 62 that calculates a difference value of the signal strengths acquired by the acquisition antenna 4, a determining unit 63 that determines whether or not to perform a position information estimation process based on the difference value, a position information estimating unit 64 that estimates the position information of the capsule endoscope 3 when the determining unit 63 determines that the position information estimation process is to be performed, a storage unit 65 that stores the image data and the signal strengths received from the capsule endoscope 3, an output unit 66 that is configured using a display, a printer, a speaker, and the like, and an input unit 67 that acquires information from the operation input device 6b or the like that is configured using a keyboard, a mouse, and the like. The storage unit 65 is configured using a hard disk that stores information magnetically and a memory that loads various programs according to this embodiment associated with a process executed by the body-insertable apparatus system 1 from the hard disk when the body-insertable apparatus system 1 executes the process, and stores the programs electrically.

The position information estimating unit 64 acquires the largest signal strength among the signal strengths received by the respective receiving antennas of the acquisition antenna 4 to obtain the position information (antenna position and orientation) of the capsule endoscope 3 from the signal strength and estimates the position of the capsule endoscope 3 (position information estimation process).

When the cradle 6a is attached to the receiving device 5, the cradle 6a acquires image data and related data such as received signal strength information, time information, and identification information of the capsule endoscope 3 correlated with the image data and transmits various items of the acquired data to the information processing device 6.

The operation input device 6b receives the input of a user. The user operates the operation input device 6b to observe a biological region (for example, the esophagus, the stomach, the small intestine, the large intestine, and the like) of the subject 2 while seeing the in-vivo images of the subject 2 sequentially displayed by the information processing device 6 to thereby diagnose the subject 2.

Figure 3:
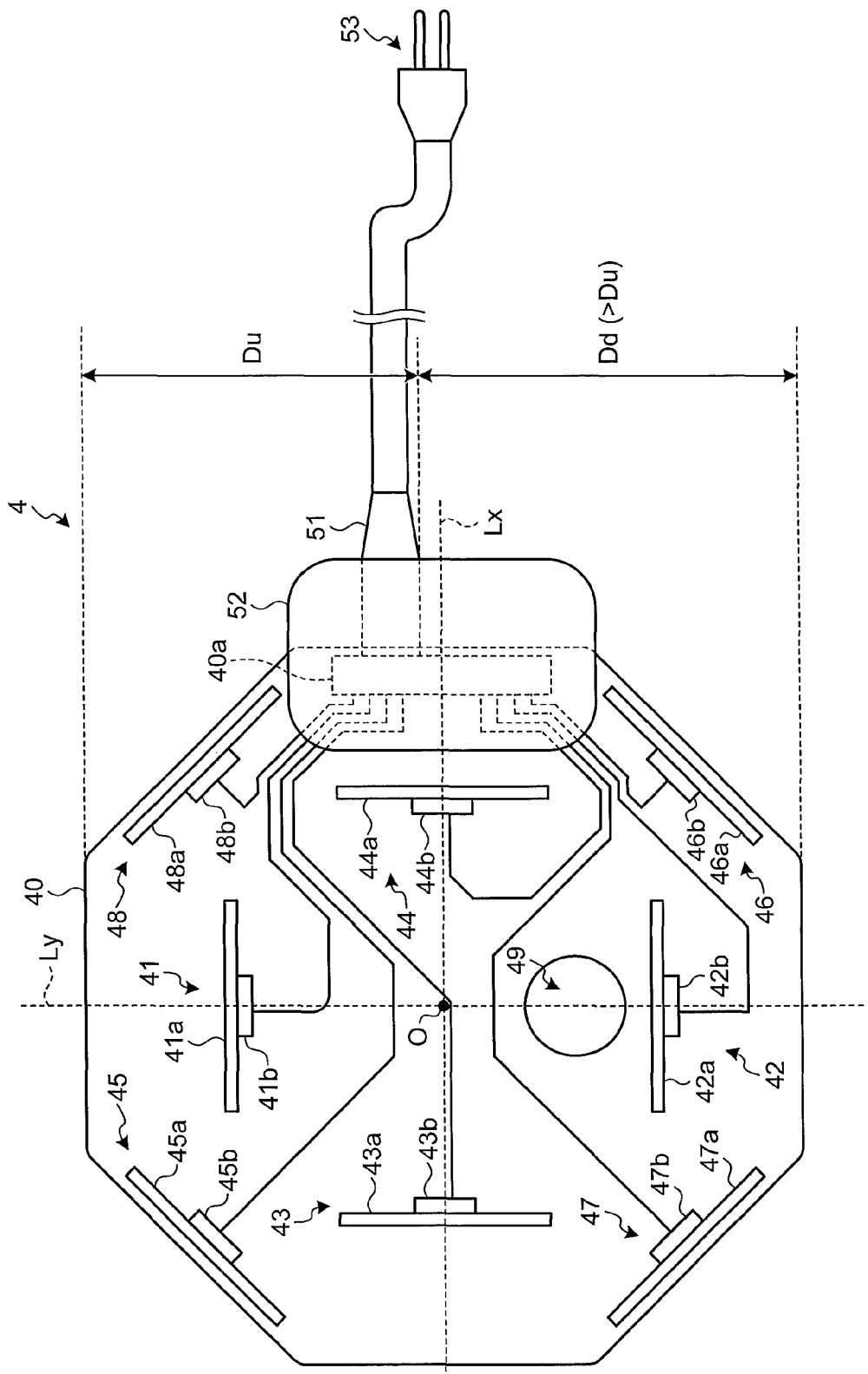
FIG. 3 is a schematic view illustrating a configuration of an acquisition antenna illustrated in FIG. 1.

Next, a detailed configuration of the acquisition antenna 4 illustrated in FIG. 1 will be described. FIG. 3 is schematic view illustrating a configuration of the acquisition antenna 4 illustrated in FIG. 1. As illustrated in FIG. 3, the acquisition antenna 4 includes a polygonal sheet portion 40, a connector portion 40a to which the antenna cable 51 is connected, a first receiving antenna 41, a second receiving antenna 42, a third receiving antenna 43, a fourth receiving antenna 44, a fifth receiving antenna 45, a sixth receiving antenna 46, a seventh receiving antenna 47, and an eighth receiving antenna 48. The first to eighth receiving antennas 41 to 48 are connected to the connector portion 40a and are formed on one polygonal sheet portion 40. In FIG. 3, a reference point O is the center of the polygonal sheet portion 40. An Ly axis is an axis that passes through the reference point O and is in parallel to the extension direction of the antenna cable 51. An Lx axis is an axis that passes through the reference point O and is orthogonal to the Lx axis.

The polygonal sheet portion 40 is configured using a flexible substrate. The principal surface of the polygonal sheet portion 40 has an approximately octagonal shape. The polygonal sheet portion 40 is formed in such a size that the polygonal sheet portion 40 covers the entire surface of the belly of the subject 2. A positioning hole 49 is formed in the polygonal sheet portion 40. The positioning hole 49 is formed such that the center thereof is at a position that is separated by a predetermined distance from the reference point O of the polygonal sheet portion 40 in the downward direction in the figure along the Ly axis. The positioning hole 49 functions as an alignment portion that determines the attachment position of the acquisition antenna 4 in relation to the subject 2 when the acquisition antenna 4 is attached to the subject 2. For example, when the polygonal sheet portion 40 is attached to the subject 2 so that an index region (for example, the navel) on the body surface of the subject 2 is positioned in a central portion of the positioning hole 49, the first to eighth receiving antennas 41 to 48 of the acquisition antenna 4 are accurately attached to a predetermined attachment position on the body surface of the subject 2. That is, by disposing antennas based on an index region on the body surface of the subject, the antennas can be disposed with high accuracy in relation to the positions of the respective antennas relative to the internal lumen, which is the internal organ of the subject 2, and through which the capsule endoscope 3 passes. Thus, by a simple operation of attaching the acquisition antenna 4 to the subject 2 using the positioning hole 49, it is possible to easily perform alignment of the acquisition antenna 4 with respect to the subject 2. A transparent member, for example, a vinyl sheet may be provided on the positioning hole 49. Moreover, the principal surface of the polygonal sheet portion 40 may not have an approximately octagonal shape but may have a quadrangular shape, for example.

The connector portion 40a is connected to the antenna cable 51 inside a connecting member 52. The antenna cable 51 has a configuration in which wires connected to the first to eighth receiving antennas 41 to 48 are bundled. A connection plug 53 is connected to the receiving device 5 by being inserted into a connecting portion on the side of the receiving device 5. The wireless signals received by the first to eighth receiving antennas 41 to 48 of the acquisition antenna 4 are output to the receiving device 5 via the antenna cable 51 connected to the connector portion 40a. A base end portion of the antenna cable 51 extends from one side of the polygonal sheet portion 40 on which the connector portion 40a is formed. In the example illustrated in FIG. 3, the antenna cable 51 extends toward the right direction in the figure. The base end portion of the antenna cable 51 is disposed at a position that is separated by a predetermined distance in the upward direction in the figure from the Lx axis rather than being disposed on the Lx axis that passes through the reference point O, and the antenna cable 51 extends in parallel to the Lx axis from the base end portion. In other words, the base end portion of the antenna cable 51 is disposed at a position that is deviated from a line that passes through the center of the polygonal sheet portion 40 and extends in parallel to the extension direction of the antenna cable 51. Thus, a length Dd between the antenna cable 51 and the lower end in the figure, of the polygonal sheet portion 40 along the Ly axis is larger than a length Du between the upper end in the figure, of the polygonal sheet portion 40 and the antenna cable 51 along the Ly axis.

The first and second receiving antennas 41 and 42 are disposed at such positions that the antennas face each other with the reference point O of the polygonal sheet portion 40 interposed. The first and second receiving antennas 41 and 42 are disposed at such positions that are separated by an equal distance from the reference point O. The first and second receiving antennas 41 and 42 include element portions 41a and 42a, respectively, which are formed on the polygonal sheet portion 40 as printed wires. The first and second receiving antennas 41 and 42 include active circuits 41b and 42b, respectively, which are connected to the element portions 41a and 42a, respectively. The active circuits 41b and 42b are formed on the polygonal sheet portion 40 as planar circuits. The active circuits 41b and 42b perform an amplification process including impedance matching of the first and second receiving antennas 41 and 42, amplification and attenuation of the received wireless signals, a conversion process of converting a balanced state to an unbalanced state, and other processes. The first and second receiving antennas 41 and 42 are connected to the connector portion 40a that is formed in the polygonal sheet portion 40 by a planar transmission line (strip-line).

The third and fourth receiving antennas 43 and 44 are disposed such positions that the antennas are rotated by 90° within a plane around the reference point O in relation to the first and second receiving antennas 41 and 42. The third and fourth receiving antennas 43 and 44 include element portions 43a and 44a, respectively, which are formed on the polygonal sheet portion 40 as printed wires. The third and fourth receiving antennas 43 and 44 include active circuits 43b and 44b, respectively, which are connected to the element portions 43a and 44a, respectively. The third and fourth receiving antennas 43 and 44 are connected to the connector portion 40a by a planar transmission line.

The fifth and sixth receiving antennas 45 and 46 are disposed at such positions that the antennas are rotated by 45° within a plane around the reference point O in relation to the first and second receiving antennas 41 and 42. The fifth and sixth receiving antennas 45 and 46 are disposed at positions closer to the outer circumference side within the plane more than the first and second receiving antennas 41 and 42. The fifth and sixth receiving antennas 45 and 46 include element portions 45a and 46a, respectively, which are formed on the polygonal sheet portion 40 by printed wires. The fifth and sixth receiving antennas 45 and 46 include active circuits 45b and 46b, respectively, which are connected to the element portions 45a and 46a, respectively. The fifth and sixth receiving antennas 45 and 46 are connected to the connector portion 40a by a planar transmission line.

The seventh and eighth receiving antennas 47 and 48 are disposed at such positions that the antennas are rotated by 90° within a plane around the reference point O in relation to the fifth and sixth receiving antennas 45 and 46. The seventh and eighth receiving antennas 47 and 48 are disposed at positions closer to the outer circumference side within the plane more than the first and second receiving antennas 41 and 42. The seventh and eighth receiving antennas 47 and 48 include element portions 47a and 48a, respectively, which are formed on the polygonal sheet portion 40 as printed wires. The seventh and eighth receiving antennas 47 and 48 include active circuits 47b and 48b, respectively, which are connected to the element portions 47a and 48a, respectively. The seventh and eighth receiving antennas 47 and 48 are connected to the connector portion 40a by a planar transmission line.

Figure 4:
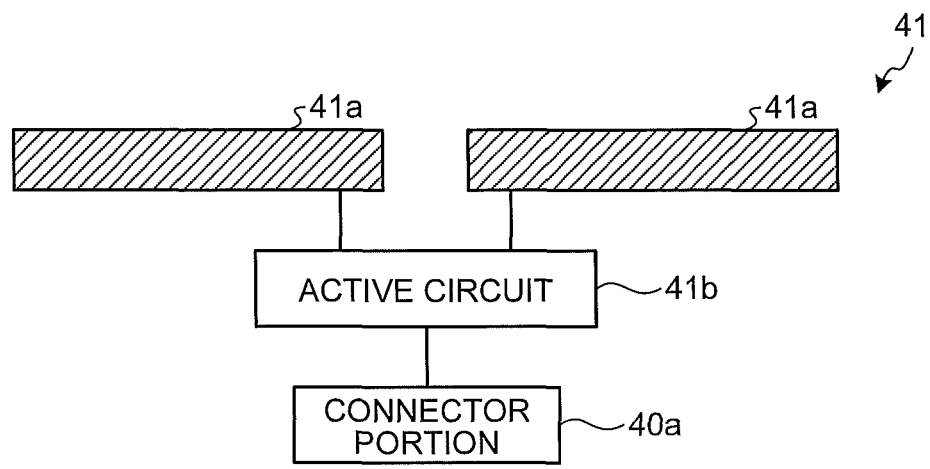
FIG. 4 is a block diagram illustrating a configuration of a first receiving antenna illustrated in FIG. 3.

Next, a configuration of the first receiving antenna 41 described in FIG. 3 will be described in detail. FIG. 4 is a block diagram illustrating a configuration of the first receiving antenna 41 illustrated in FIG. 3.

As illustrated in FIG. 4, the first receiving antenna 41 is configured using a balanced antenna. Specifically, the first receiving antenna 41 is configured using a dipole antenna in which the element portion 41a includes two linear lead wires. The first receiving antenna 41 is formed such that the two linear lead wires of the element portion 41a are formed bilaterally symmetrically in the same length on a straight line. Due to this, in the first receiving antenna 41, a cross-polarization loss against the principal polarized wave increases. The second to eighth receiving antennas 42 to 48 have the same configuration as the first receiving antenna 41, and description thereof will not be provided. Moreover, in the first embodiment, although the number of receiving antennas is 8, the number is not limited to 8.

Here, the acquisition antenna 4 is attached to the body surface of the subject 2 in such a manner that a predetermined antenna holder is fixed to the subject 2 by the belt of the antenna holder in a state where the acquisition antenna 4 is held in the antenna holder. Next, the antenna holder that holds the acquisition antenna 4 will be described.

Figure 5:
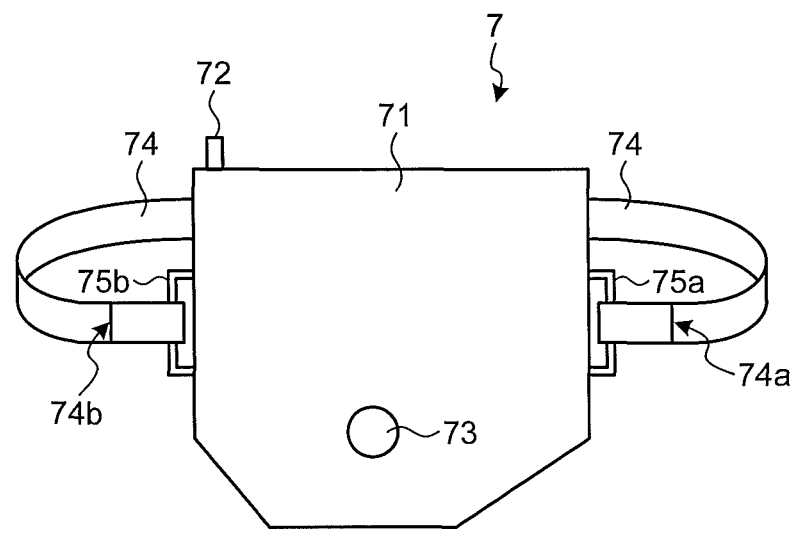
FIG. 5 is a front view of an antenna holder that holds the acquisition antenna illustrated in FIG. 1.
Figure 6:
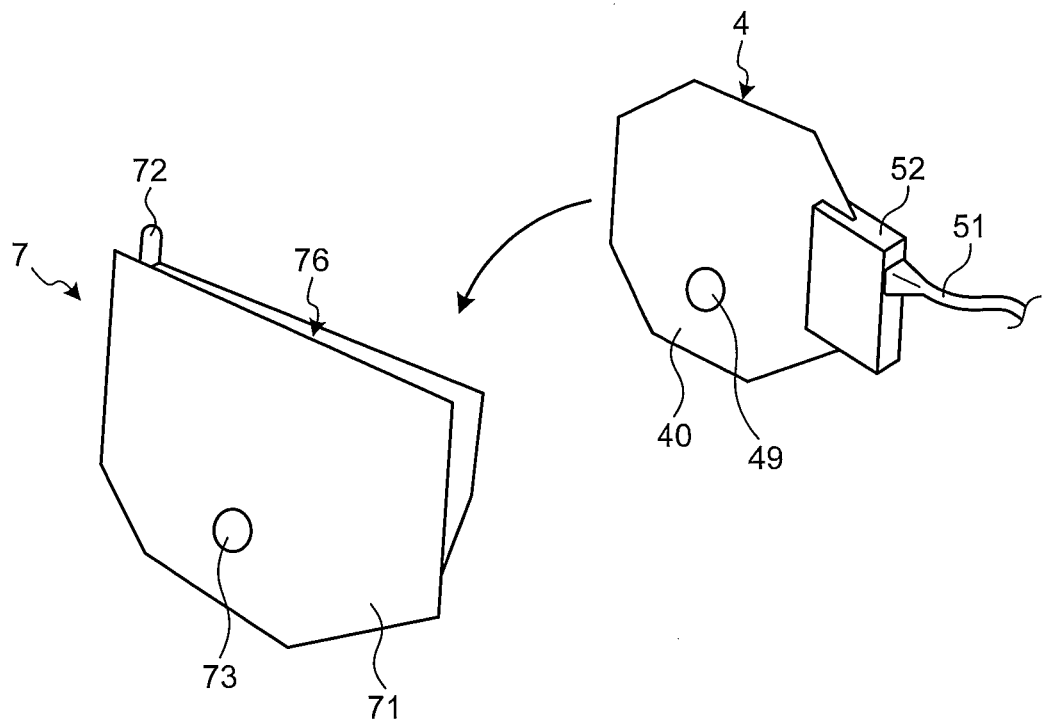
FIG. 6 is a schematic view for describing accommodation of the acquisition antenna in a container portion illustrated in FIG. 5.
Figure 7:
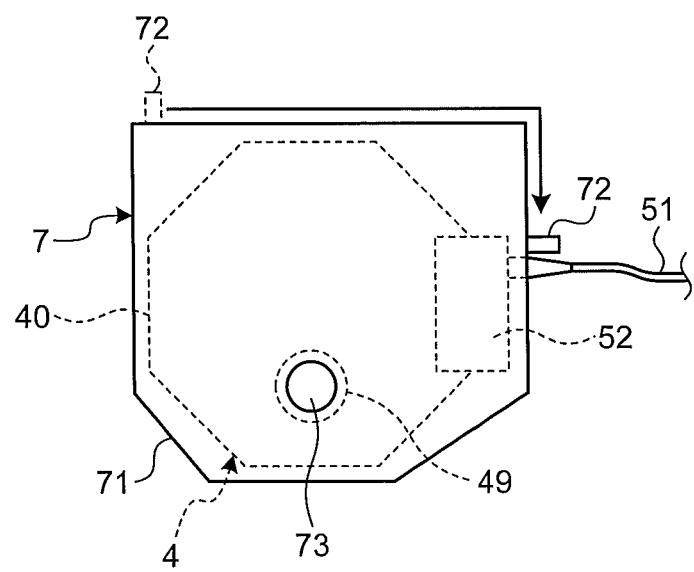
FIG. 7 is a front view of the container portion illustrated in FIG. 5 in which the acquisition antenna is held.

FIG. 5 is a front view of the antenna holder that holds the acquisition antenna 4 illustrated in FIG. 1. FIG. 5 illustrates a surface of an antenna holder 7 that faces the outer side of the subject 2 when the antenna holder 7 is attached to the subject 2. FIG. 6 is a schematic view for describing accommodation of the acquisition antenna 4 in the antenna holder 7 illustrated in FIG. 5. FIG. 7 is a front view of the antenna holder 7 in which the acquisition antenna 4 is held. FIGS. 6 and 7 illustrate only the main parts of the antenna holder 7 illustrated in FIG. 5.

As illustrated in FIG. 5, the antenna holder 7 that holds the acquisition antenna 4 illustrated in FIG. 1 includes a container portion 71 that has an outer surface shape corresponding to the shape of the acquisition antenna 4 and is configured to hold the acquisition antenna 4, one belt 74 that is detachable from the container portion 71 and is attached to the container portion 71 to fix the container portion 71 to the subject 2, and ring-shaped belt loops 75a and 75b that are connected to the right and left sides of the container portion 71. Respective end portions 74a and 74b of the belt 74 pass through the ring-shaped belt loops 75a and 75b.

As illustrated in FIGS. 5 and 6, the container portion 71 has such a pouch shape that the acquisition antenna 4 can be inserted in the pouch and that has an opening 76 that can be open and closed. The container portion 71 is configured such that the entire upper side in the figure and a partial right side in the figure are open and closed according to opening and closing of a fastener. The opening length and width of the opening 76 of the container portion 71 are set to such opening length and width that the acquisition antenna 4 can be inserted. Moreover, a positioning hole 73 is formed in the container portion 71 at a position corresponding to the positioning hole 49 of the acquisition antenna 4 that is to be held. That is, the positioning hole 73 is formed such that the center thereof is located at the position corresponding to the center of the positioning hole 49 of the acquisition antenna 4 when the acquisition antenna 4 is inserted and the fastener is closed. In order to prevent a catch of the finger of an operator during the alignment, the positioning hole 73 of the container portion 71 preferably has a smaller diameter than that of the positioning hole 49 of the acquisition antenna 4.

When the acquisition antenna 4 is held in the antenna holder 7, first, a slider 72 that opens and closes the fastener is moved to open the fastener, whereby the container portion 71 is open so that the polygonal sheet portion 40 of the acquisition antenna 4 can be inserted, and then, the acquisition antenna 4 is held in the opening 76 as indicated by an arrow in FIG. 6. When the antenna holder 7 is seen from the front, the acquisition antenna 4 is held in the opening 76 so that the antenna cable 51 connected to the acquisition antenna 4 extends from the right side of the antenna holder 7. Here, on a side corresponding to one side of the polygonal sheet portion 40 to which the base end portion of the antenna cable 51 is connected, when the polygonal sheet portion 40 is held in a correct orientation, the base end portion of the antenna cable 51 connected to the polygonal sheet portion 40 is positioned at an end portion of the opening 76 of the container portion 71. That is, on the side corresponding to one side of the polygonal sheet portion 40 to which the base end portion of the antenna cable 51 is connected, the slider 72 stops at the position corresponding to the base end portion of the antenna cable 51. On this side, the container portion 71 is open to only a position that corresponds to a position that is separated by a predetermined distance in the upward direction in the figure from the Lx axis of the polygonal sheet portion 40 of the acquisition antenna 4.

After that, the slider 72 is moved to close the fastener as indicated by an arrow in FIG. 7. When the polygonal sheet portion 40 is held in the container portion 71 of the antenna holder 7 in a correct orientation, the positioning hole 49 of the polygonal sheet portion 40 of the acquisition antenna 4 overlaps the positioning hole 73 of the container portion 71 of the antenna holder 7. At the overlapped position of both positioning holes 49 and 73, since the front and rear surfaces of the antenna holder 7 are penetrated, the user can visually perceive the subject 2 located on the rear surface side of the antenna holder 7 from the front surface side of the antenna holder 7.

Figure 8:
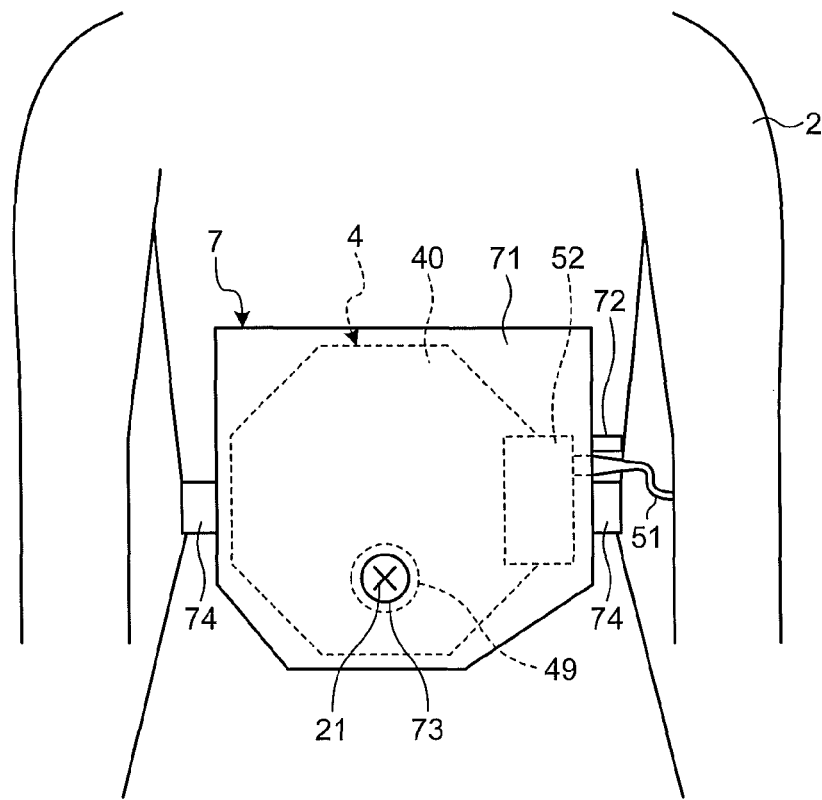
FIG. 8 is a view for describing attachment to a subject, of the antenna holder illustrated in FIG. 5 in which the acquisition antenna is held.

Thus, when the acquisition antenna 4 is attached to the subject 2, the position of the antenna holder 7 is adjusted so that an index region on the body surface of the subject 2 can be seen through the overlapped positioning holes 49 and 73, and the antenna holder 7 is fixed to the subject 2 using the belt 74. For example, in order to capture the image of the small intestine of the subject 2 using the capsule endoscope 3, the first to eighth receiving antennas 41 to 48 need to be disposed at positions corresponding to the position of the small intestine. In this case, the navel near the small intestine is selected as the index region that can be visually perceived from the body surface of the subject 2. Thus, as illustrated in FIG. 8, the arrangement position of the antenna holder 7 is adjusted so that the navel 21 of the subject 2 is visible through the overlapped positioning holes 49 and 73 and the navel 21 is positioned at the center of the positioning holes 49 and 73. When the adjustment ends, subsequently, the antenna holder 7 is fixed to the subject 2 using the belt 74.

In this manner, in the first embodiment, the positioning holes 49 and 73 are formed so that when the polygonal sheet portion 40 of the acquisition antenna 4 is held in the antenna holder 7 in a correct orientation, the positioning hole 49 of the acquisition antenna 4 overlaps the positioning hole 73 of the antenna holder 7. Moreover, the position of the positioning hole 49 is set such that when the polygonal sheet portion 40 is attached to the subject 2 so that the index region of the subject 2 is positioned within the positioning hole 49, the first to eighth receiving antennas 41 to 48 of the polygonal sheet portion 40 are accurately attached at a predetermined attachment position on the body surface of the subject 2. Thus, the operator can attach all of the first to eighth receiving antennas 41 to 48 of the acquisition antenna 4 to the subject 2 at an appropriate accurate position by just adjusting the position of the antenna holder to attach the antenna holder 7 to the subject 2 so that the index region is positioned within the overlapped positioning holes 49 and 73. When the positioning hole 49 is penetrated, and a transparent member or the like is not provided, since the operator can directly contact the navel 21, it is possible to perform alignment while contacting the navel 21.

Figure 9:
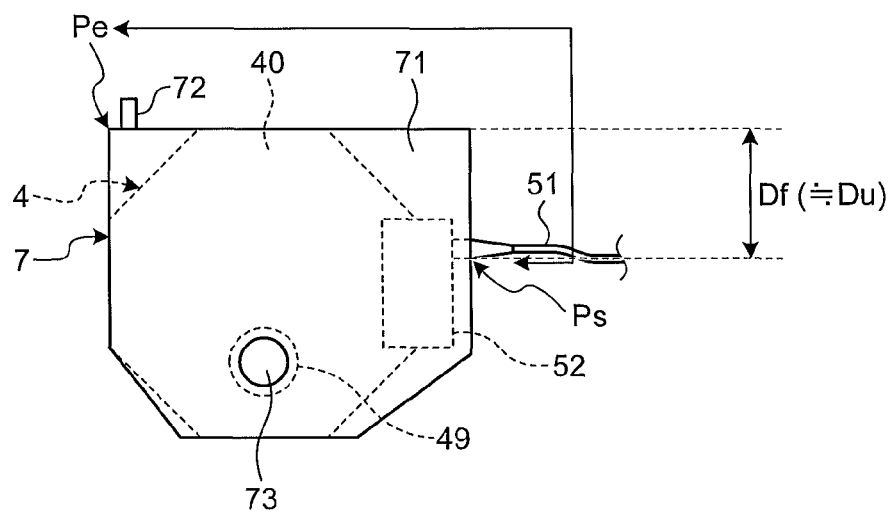
FIG. 9 is a front view of the container portion illustrated in FIG. 5 in which the acquisition antenna is held.

Moreover, as illustrated in FIG. 9, the container portion 71 of the antenna holder 7 is configured such that the entire upper side and a partial upper side in the figure are open and closed according to the opening and closing of the fastener. Specifically, the slider 72 can move from a fastener end portion Ps to another fastener end portion Pe. The slider 72 opens the container portion 71 by moving from the fastener end portion Ps to the fastener end portion Pe. The slider 72 closes the opening of the container portion 71 by moving from the fastener end portion Pe to the fastener end portion Ps.

Here, as described in FIG. 3, the base end portion of the antenna cable 51 is disposed at such a position that passes through the center of the polygonal sheet portion 40 and is deviated from the Lx axis that is parallel to the extension direction of the antenna cable 51. That is, the length Dd between the antenna cable 51 and the lower end in the figure, of the polygonal sheet portion 40 along the Ly axis is larger than the length Du between the upper end in the figure, of the polygonal sheet portion 40 and the antenna cable 51 along the Ly axis. Here, the fastener end portion Ps of the container portion 71 is disposed at a position corresponding to an extension position of the antenna cable 51 from the polygonal sheet portion 40. A length Df between the upper end of the container portion 71 and the fastener end portion Ps is approximately the same as the length Du. In other words, the length Df between the upper end of the container portion 71 and the end portion Ps is shorter than the length Dd.

Thus, when the polygonal sheet portion 40 of the acquisition antenna 4 is inserted in a correct orientation, as illustrated in FIG. 9, the entire polygonal sheet portion 40 is held inside the container portion 71, and no part of the polygonal sheet portion 40 will protrude outside the container portion 71.

Figure 10:
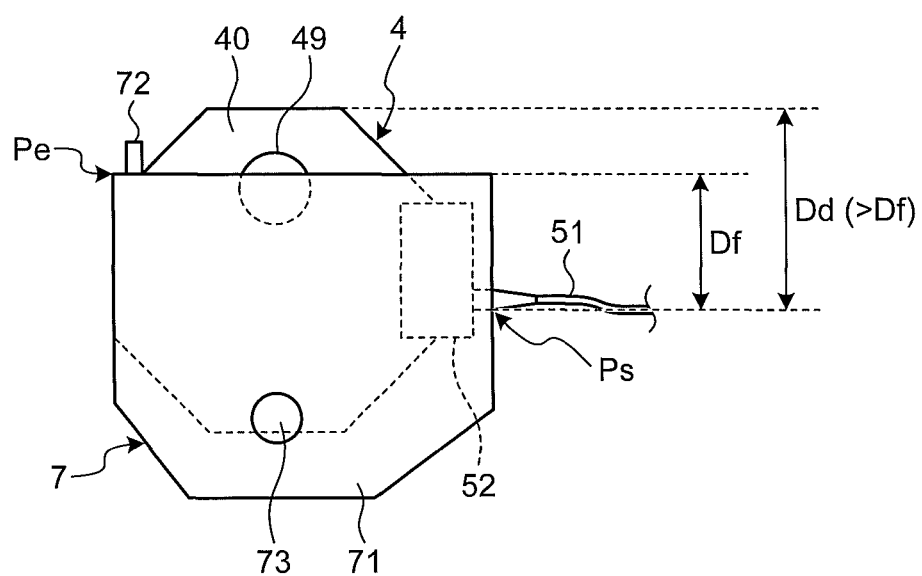
FIG. 10 is a front view of the container portion illustrated in FIG. 5 in which the acquisition antenna is held in a reversed state.

In contrast, when the polygonal sheet portion 40 of the acquisition antenna 4 is inserted in the container portion 71 in a reversed state, as illustrated in FIG. 10, as illustrated in FIG. 10, the antenna cable 51 is caught at the fastener end portion Ps before the entire polygonal sheet portion 40 is held in the container portion 71, and the entire polygonal sheet portion 40 is not received. Thus, a part of the polygonal sheet portion 40 protrudes from the upper side of the container portion 71, and it is not possible to close the fastener of the container portion 71. Thus, when the operator inserts the acquisition antenna 4 in the antenna holder 7 in a reversed state, since the polygonal sheet portion 40 of the acquisition antenna 4 protrudes from the antenna holder 7, and the fastener of the antenna holder 7 may not be closed, the operator can easily recognize that the acquisition antenna 4 is inserted in the antenna holder 7 in a reversed state in error.

Moreover, when the polygonal sheet portion 40 of the acquisition antenna 4 is inserted in the container portion 71 in a reversed state, the arrangement position of the positioning hole 49 of the polygonal sheet portion 40 in relation to the positioning hole 73 of the antenna holder 7 is reversed in relation to the reference point O. Thus, as illustrated in FIG. 10, the positioning hole 73 of the antenna holder 7 is blocked by the polygonal sheet portion 40. When the operator inserts the acquisition antenna 4 in the antenna holder 7 in a reversed state, since the positioning hole 73 of the antenna holder 7 is blocked, it is not possible to check the index region of the subject 2 through the positioning hole 73. Thus, the operator can easily recognize that the acquisition antenna 4 is inserted in the antenna holder 7 in a reversed state in error.

When the polygonal sheet portion 40 of the acquisition antenna 4 is attached to the subject 2 in a reversed state, since the positional relationship between the first to eighth receiving antennas 41 to 48 is reversed, it is not possible to correctly estimate the position information of the capsule endoscope 3.

In the first embodiment, in a state where the acquisition antenna 4 is held in the container portion 71 to perform alignment between the positioning hole 49 and the positioning hole 73, since the base end portion of the antenna cable 51 is positioned at the end portion of the opening 76, it is possible to easily recognize that the acquisition antenna 4 is inserted in the antenna holder 7 in a reversed state in error. It is possible to prevent the first to eighth receiving antennas 41 to 48 from being attached to the subject 2 at an incorrect position and to estimate the correct position information of the capsule endoscope 3.

In the example illustrated in FIG. 3, although a case where the positioning hole 49 is formed at such a position that the center is separated by a predetermined distance in the downward direction along the Ly axis from the reference point O of the polygonal sheet portion 40 so that the navel 21 can be visually perceived has been described as an example, the present invention is not limited to this. Without being limited to the navel 21, an index region on the body surface having high relative positional correlation with the position of an image acquisition target organ of the subject 2 may be set so as to correspond to the image acquisition target organ, and the formation position of the positioning hole 49 may be determined so as to correspond to the index region and the attachment position of the first to eighth receiving antennas 41 to 48. Moreover, the position of the positioning hole 73 of the antenna holder 7 may be set so as to correspond to the position of the positioning hole 49 of the polygonal sheet portion 40.

Figure 11:
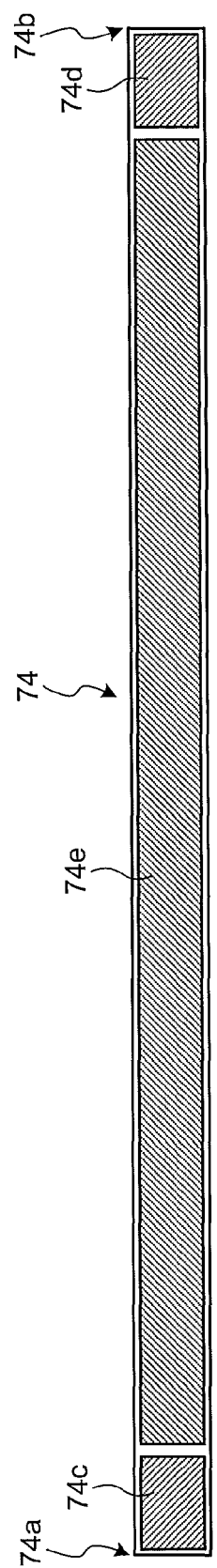
FIG. 11 is a view illustrating one surface of a belt illustrated in FIG. 5.

Next, the belt 74 illustrated in FIG. 5 will be described. FIG. 11 is a view illustrating one surface of the belt 74 illustrated in FIG. 5. As illustrated in FIG. 11, a hook surface of a hook-and-loop fastener is formed in predetermined portions 74c and 74d on both ends of one surface of the belt 74, and a loop surface of the hook-and-loop fastener is formed in the other portion 74e. The hook-and-loop fastener is not formed on the other surface of the belt 74.

Figure 12:
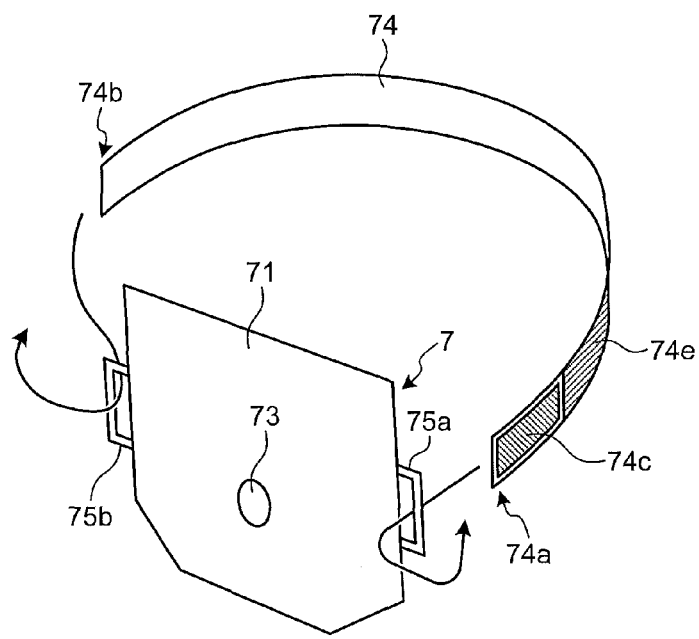
FIG. 12 is a view for describing attachment of the belt illustrated in FIG. 11 to the container portion illustrated in FIG. 5.

When the body of the antenna holder 7 is attached to the subject 2, as illustrated in FIG. 12, the end portions 74a and 74b are passed through the belt loops 75a and 75b so that the surface where the hook-and-loop fastener is formed is on the outer side. After that, the length of the belt 74 passed through the belt loops 75a and 75b is adjusted so that the length of the belt 74 fits to the abdominal circumference of the subject 2, and the end portions 74a and 74b are folded back to fix the belt 74 using the hook-and-loop fastener.

When the belt 74 is configured as illustrated in FIG. 11, since the hook-and-loop fastener is formed on the entire surface of the belt 74, it is possible to finely adjust a fastening strength of the belt 74 so as to fit to the abdominal circumference of each subject 2. Moreover, after the belt 74 is passed through the belt loops 75a and 75b, just by folding back the end portions of the belt 74 and pressing the end portions onto the belt 74 itself, it is possible to easily fix the acquisition antenna 4 to the subject 2. Thus, by configuring the belt 74 as illustrated in FIG. 11, it is possible to easily perform a series of operations of adjusting the fastening strength of the belt 74 and fixing the belt 74 and to reduce the burden of the subject 2 when attaching the acquisition antenna 4. Moreover, in this case, it is possible to deal with a case where a fluctuation of the abdominal circumferences is large.

Moreover, since the belt 74 is configured to be detachable from the body of the antenna holder 7, by preparing plural belts 74 having different lengths, it is possible to deal with attachment of the acquisition antenna 4 to subjects 2 having various abdominal circumferences.

Figure 13:
FIG. 13 is a view illustrating a rear surface of another example of the belt illustrated in FIG. 5.
Figure 14:
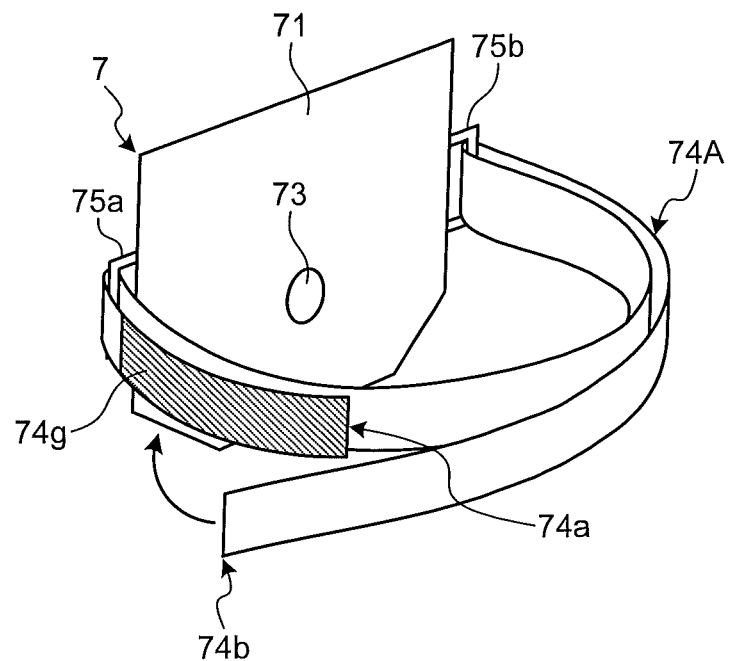
FIG. 14 is a view for describing attachment of the belt illustrated in FIG. 13 to the container portion illustrated in FIG. 5.

Moreover, as in a belt 74A illustrated in FIG. 13, the same hook-and-loop fastener as that of the belt 74 may be formed on a front surface, and a loop surface of the hook-and-loop fastener may be formed in a portion 74g on the rear surface closer to one end portion 74a so that as illustrated in FIG. 14, the end portion 74b that is folded back after being passed through the belt loop 75b can be fixed by the loop surface of the portion 74g on the rear surface closer to the end portion 74a. In this way, it is possible to deal with the subject 2 having a smaller abdominal circumference.

Figure 15A:
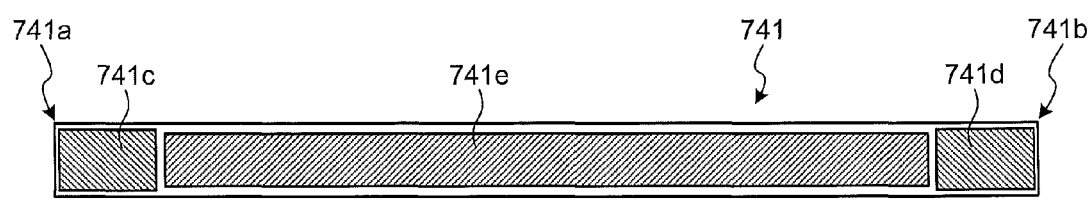
FIG. 15A is a view illustrating a front surface of a connecting belt.
Figure 15B:
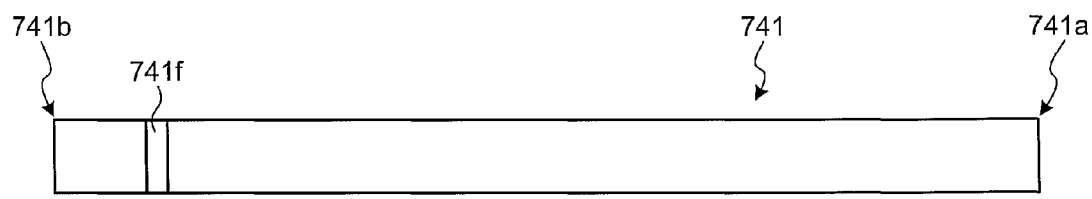
FIG. 15B is a view illustrating a rear surface of the connecting belt.

Further, when belts are configured to be connected to each other, it is possible to deal with a wide range of abdominal circumferences of the subject 2 with a small number of belts. Specifically, a connecting belt will be described. FIG. 15A is a view illustrating a front surface of a connecting belt. FIG. 15B is a view illustrating a rear surface of a connecting belt.

Figure 16:
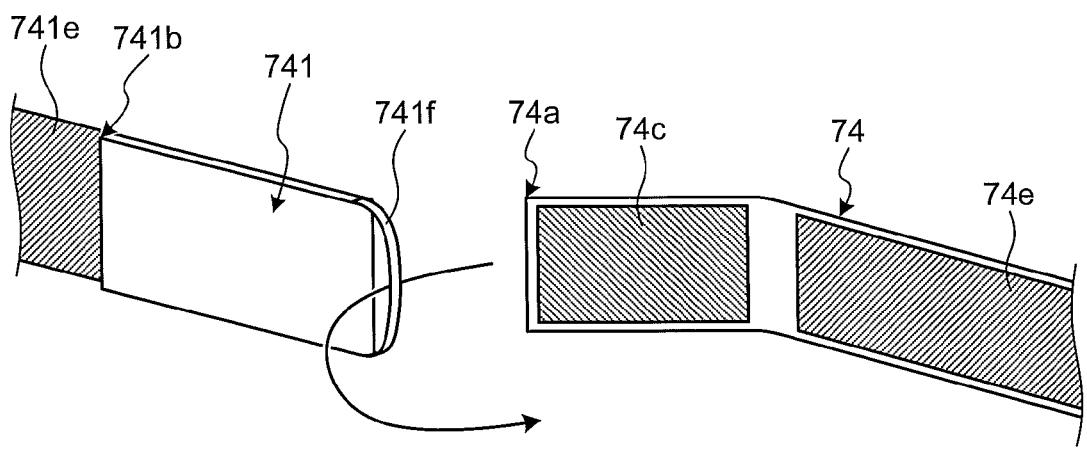
FIG. 16 is a view for describing a method of connecting the connecting belt illustrated in FIGS. 15A and 15B to the belt illustrated in FIG. 11.
Figure 17:
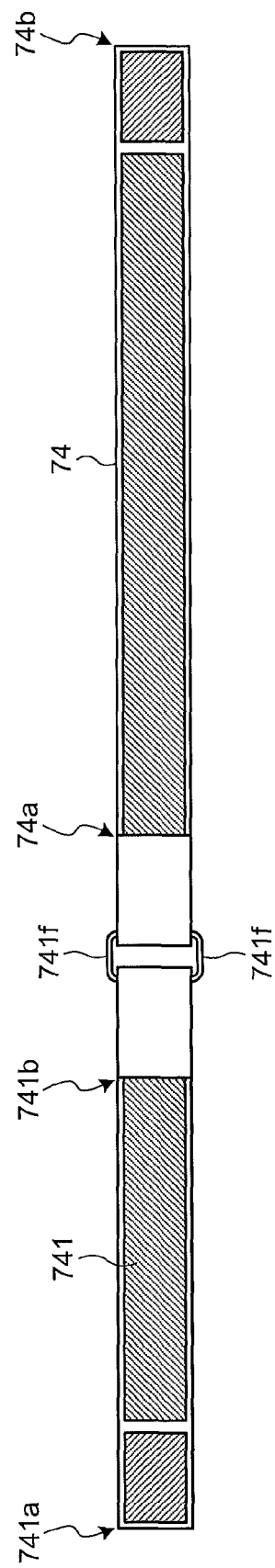
FIG. 17 is a view illustrating a state in which the connecting belt illustrated in FIGS. 15A and 15B is connected to the belt illustrated in FIG. 11.

As illustrated in FIGS. 15A and 15B, similarly to the belt 74, the hook surface of a hook-and-loop fastener is formed in predetermined portions 741c and 741d on the front surface of a connecting belt 741 closer to both end portions 741a and 741b, and the loop surface of the hook-and-loop fastener is formed in the other portion 741e. Moreover, a ring-shaped belt loop 741f is formed on the rear surface of the connecting belt 741. As illustrated in FIG. 16, in a state where the surface of the belt 74 where the hook-and-loop fastener is formed faces the same side as the front surface of the connecting belt 741, the end portion 74a of the belt 74 is passed through the belt loop 741f of the connecting belt 741. After that, the end portion 74a of the belt is folded back and is pressed and fixed onto the portion 74e in which the loop surface of the hook-and-loop fastener is formed. In the connecting belt 741, the end portion 741b is folded back and is pressed and fixed onto the portion 741e in which the loop surface of the hook-and-loop fastener is formed. As a result, as illustrated in FIG. 17, the belt 74 is connected to the connecting belt 741, and a belt that is longer than the belt 74 can be obtained. When the connecting belt 741 is shorter than the belt 74, just by preparing the belt 74 and the connecting belt 741, it is possible to select one from three types of belts with different lengths, which include a belt with a standard length, a belt having a smaller length than the standard length, and a belt having a larger length than the standard length.

Second Embodiment

Figure 18:
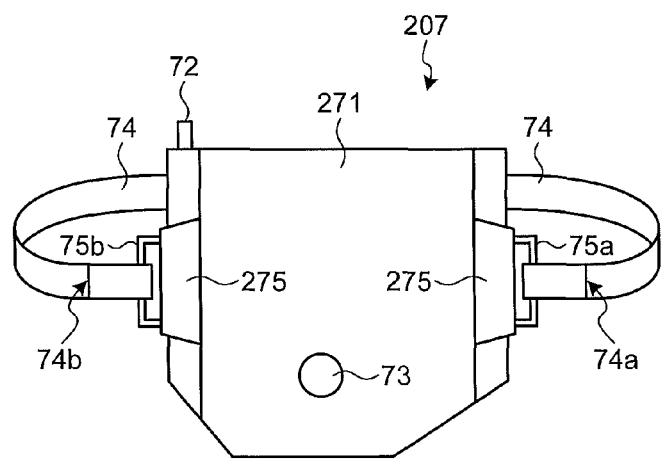
FIG. 18 is a front view of an antenna holder according to a second embodiment.

Next, a second embodiment will be described. FIG. 18 is a front view of an antenna holder according to the second embodiment. FIG. 18 illustrates a surface of the antenna holder according to the second embodiment that faces the outer side of the subject 2 when the antenna holder is attached to the subject 2.

As illustrated in FIG. 18, an antenna holder 207 according to the second embodiment has a configuration in which the antenna holder 207 includes a container portion 271 that is configured to hold the acquisition antenna 4, and belt loops 75a and 75b are formed in connecting portions 275 that are attached to both sides of the container portion 271.

Figure 19:
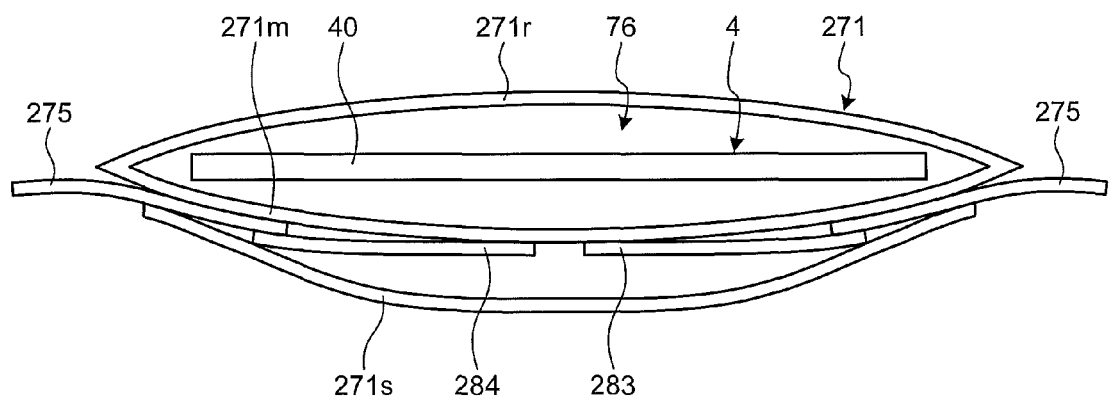
FIG. 19 is a view of a container portion illustrated in FIG. 18 when seen from the above.

FIG. 19 is a view of the container portion 271 illustrated in FIG. 18 when seen from the above. FIG. 19 illustrates only the main parts of the open container portion 271. As illustrated in FIG. 19, the container portion 271 has a three-layer structure that includes a rearmost layer 271r, a middle layer 271m, and a surface layer 271s.

The rearmost layer 271r and the middle layer 271m form such a pouch shape that the acquisition antenna 4 can be inserted in the pouch and that has an opening 76 that can be open and closed. In the container portion 271, the fastener can be open and closed in the same range of areas as in the container portion 71, and an positioning hole 73 is formed at the same position as that of the container portion 71. The connecting portions 275 are attached to both ends of the outer surface of the middle layer 271m, and one sets of ends of plural rubber bands (in FIG. 19, only rubber bands 283 and 284 are illustrated) described later are attached to the outer surface. The positioning hole 73 is formed in the surface layer 271s similarly to the rearmost layer 271r and the middle layer 271m.

Figure 20:
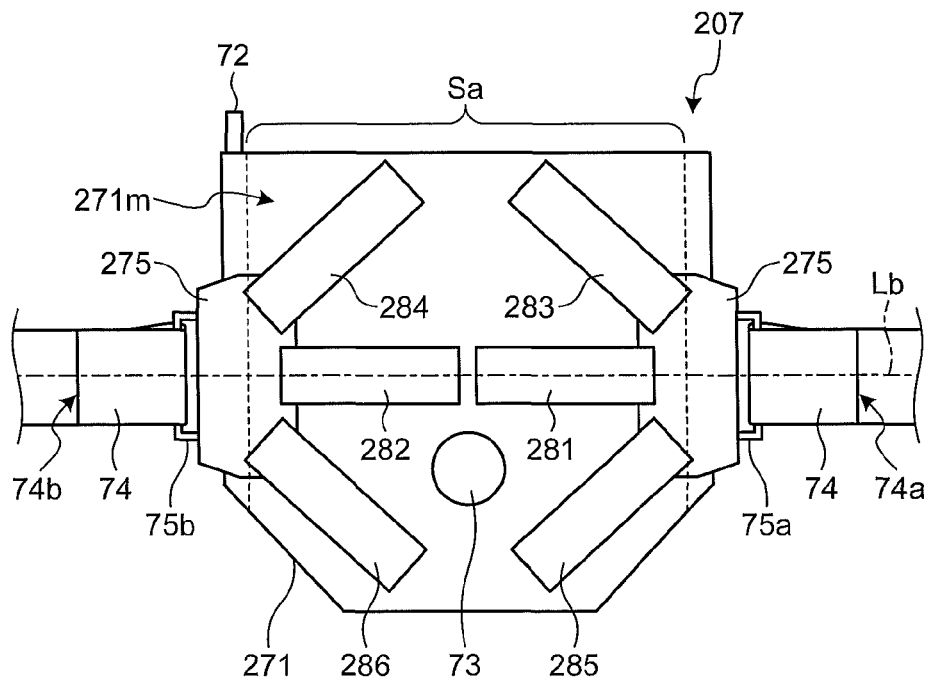
FIG. 20 is a front view of an antenna holder in a state where a surface layer is removed from the container portion illustrated in FIG. 18.

Next, plural rubber bands formed on the outer surface of the middle layer 271m will be described with reference to FIG. 20. FIG. 20 is a front view of the antenna holder 207 in a state where the surface layer 271s is removed from the container portion 271. FIG. 20 illustrates a surface of the antenna holder 207 that faces the outer side of the subject 2 when the subject 2 is attached to the antenna holder 207. The above-described surface layer 271s functions as a cover that covers a front surface area Sa of the middle layer 271m in FIG. 20 to cover rubber bands 281 to 286 and prevents an external member from being caught at the rubber bands 281 to 286.

As illustrated in FIG. 20, six rubber bands 281 to 286 are formed on the outer surface of the middle layer 271m. A set of ends that face the inner side of the container portion 271 among the both sets of ends of these rubber bands 281 to 286 are fixed to the middle layer 271m. A set of ends that face the outer side of the container portion 271, which are the other set of ends of the rubber bands 281 to 286 are fixed to the connecting portions 275 on both sides of the container portion 271. Thus, the container portion 271 and the belt 74 are connected by the rubber bands 281 to 286, the connecting portions 275, and the belt loops 75a and 75b. In other words, both sets of ends of the rubber bands 281 to 286 are directly or indirectly connected to the container portion 271 and the belt 74.

Among the rubber bands 281 to 286, the rubber bands 281 and 282 are disposed near the center of the middle layer 271m on a Lb axis which is the long axis of the extending belt 74 and extend and contract along the Lb axis. That is, the rubber bands 281 and 282 are stretchable in the extension direction of the belt 74. The plural rubber bands 283 to 286 is disposed around the rubber bands 281 and 282 so that the extension and contract direction thereof crosses the extension direction of the belt 74. Moreover, the rubber bands 284 and 286 have a symmetrical shape and are disposed in symmetrical positions in relation to the rubber band 282. The same is true for the rubber bands 283 and 285. Due to this, the rubber bands 283 to 286 are stretchable in a direction crossing the Lb axis, that is, in a direction crossing the extension direction of the belt 74.

Figure 21:
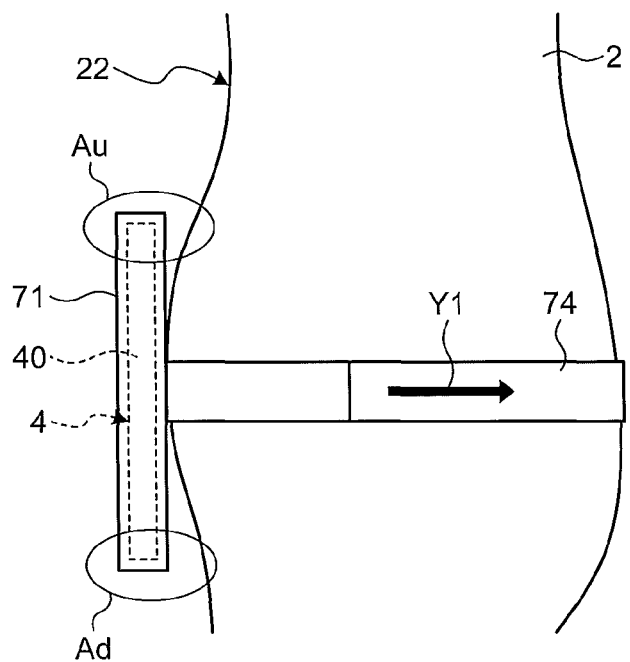
FIG. 21 is a view for describing an attachment state to a subject, of the antenna holder according to the first embodiment.

As illustrated in FIG. 21, in the antenna holder 7 according to the first embodiment, the acquisition antenna 4 is pressed against the subject 2 by only a pulling force that goes in the direction indicated by arrow Y1 which is the extension direction of the belt 74. Thus, as indicated by areas Au and Ad, the upper and lower portions of the polygonal sheet portion 40 of the acquisition antenna 4 float from a body surface 22 of the subject 2. As a result, there is a case where some of the plural receiving antennas of the acquisition antenna 4 is not closely attached.

Figure 22:
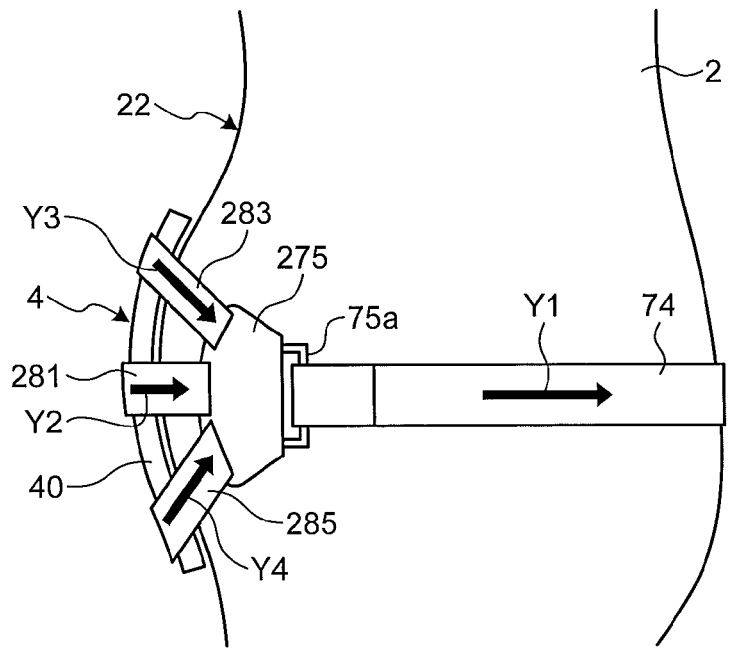
FIG. 22 is a view for describing an attachment state to a subject, of the antenna holder according to the second embodiment.

In contrast, when the acquisition antenna 4 is attached to the subject 2 using the antenna holder 207, as illustrated in FIG. 22, the two rubber bands 281 and 282 near the center presses the central portion of the polygonal sheet portion 40 against the body surface 22 as indicated by arrow Y2 according to extension of the belt 74 in the direction indicated by arrow Y1. Further, the rubber bands 283 to 286 that are connected to the belt 74 by the connecting portions 275 and the belt loops 75a and 75b also extend in the direction crossing the Lb axis according to the extension of the belt 74 and press the upper and lower portions of the polygonal sheet portion 40 against the body surface 22 so along the direction of the long axis of the belt 74 as indicated by arrows Y3 and Y4. In FIG. 22, in order to simplify the description, the container portion 271 of the antenna holder 207 is not depicted.

As a result, when the antenna holder 207 is used, the entire surface of the polygonal sheet portion 40 of the acquisition antenna 4 is attached to the subject 2 without floating from the body surface 22. Thus, according to the second embodiment, all of the first to eighth receiving antennas 41 to 48 of the polygonal sheet portion 40 are reliably closely attached to the body surface 22 of the subject 2. Thus, all receiving antennas can stably receive the wireless signal from the capsule endoscope 3, and the position information of the capsule endoscope 3 can be estimated with higher accuracy.

First Modification of Second Embodiment

Figure 23:
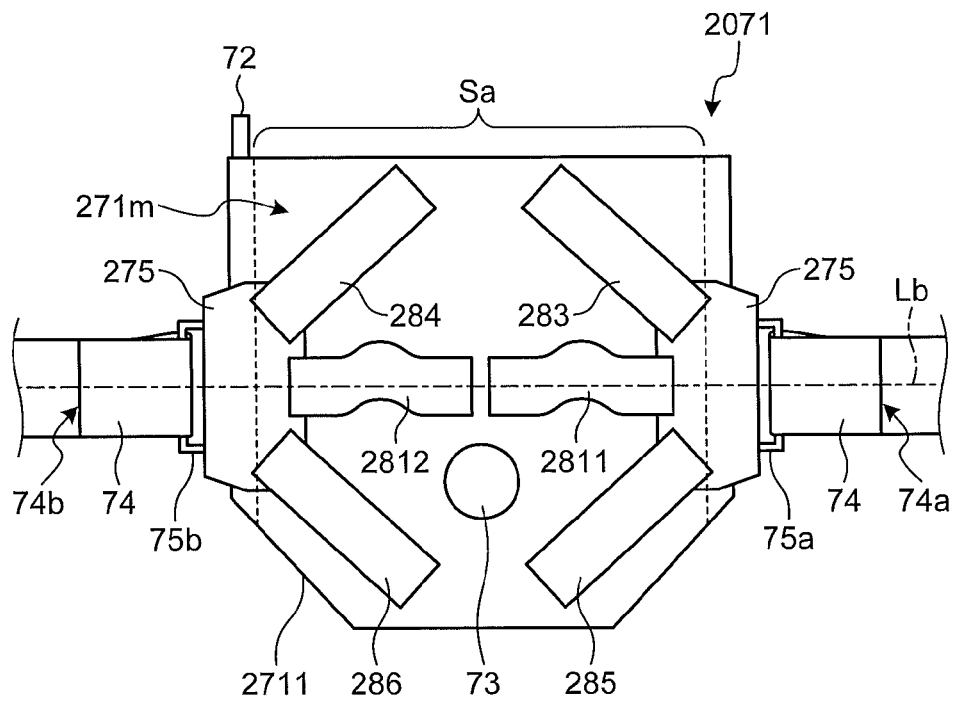
FIG. 23 is a front view of an antenna holder according to a first modification of the second embodiment.

Next, a first modification of the second embodiment will be described. FIG. 23 is a front view of an antenna holder according to the first modification of the second embodiment and illustrates a state where a surface layer is removed from a container portion of the antenna holder.

As illustrated in FIG. 23, in an antenna holder 2071 according to the first modification of the second embodiment, two rubber bands 2811 and 2812 near the center among six rubber bands that are attached to the front surface of the middle layer 271m of a container portion 2711 are connected to the middle layer 271m and the connecting portions 275 in a state of having a sagging in the direction of the Lb axis. The rubber bands 283 to 286 around the rubber bands 2811 and 2812 are connected to the middle layer 271m and the connecting portions 275 without any sagging. In other words, in a state where no load is applied from the outside, the tension of the rubber bands 283 to 286 are set to be greater than the tension of the rubber bands 2811 and 2812. For example, when the rubber bands 2811 and 2812 are formed with the same length and from the same material as the rubber bands 283 to 286, a difference between a natural length of the rubber bands 2811 and 2812 and the length between the attachment positions of both ends of the rubber bands 2811 and 2812 in relation to the antenna holder 2071 is set to be larger than the difference between a natural length of the rubber bands 283 to 286 and the length between the attachment positions of both ends of the rubber bands 283 to 286 in relation to the antenna holder 2071.

Figure 24:
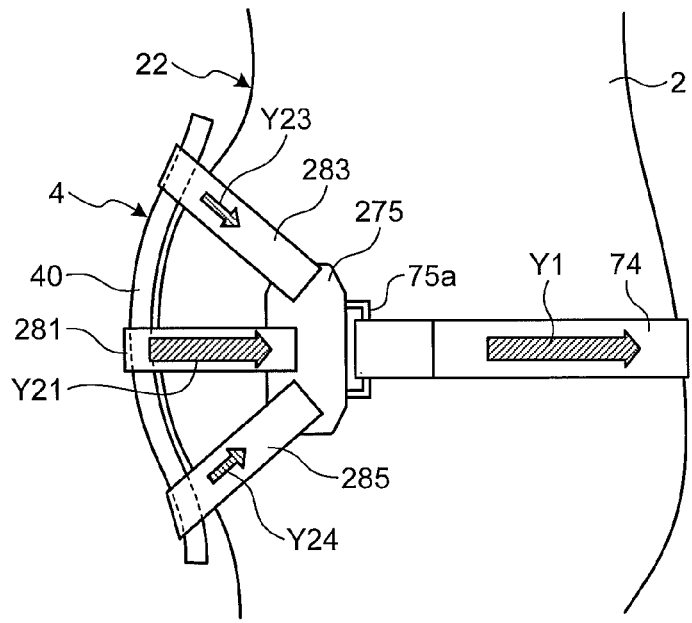
FIG. 24 is a view for describing an attachment state to a subject, of the antenna holder according to the second embodiment.

In the antenna holder 207 according to the second embodiment, all rubber bands 281 to 286 are connected to the container portion 271 and the belt 74 without any sagging. Thus, as illustrated in FIG. 24, there is a case where if the acquisition antenna is pulled in the direction indicated by arrow Y1 by the belt 74 when it is attached to the subject 2, only the rubber bands 281 and 282 of which the extension direction is identical to the extension direction of the belt 74 is strongly pulled as indicated by arrow Y21, and the rubber bands 283 to 286 of which the extension direction is not identical to the extension direction of the belt 74 are not strongly pulled as indicated by arrows Y23 and Y24. In this case, there may be case where a force sufficient to attach the acquisition antenna closely to the body surface 22 is not generated from the rubber bands 283 to 286 that are not strongly pulled, and the entire polygonal sheet portion 40 of the acquisition antenna 4 is not closely attached to the body surface 22. In FIG. 24, in order to simplify the description, the container portion 271 of the antenna holder is not depicted.

In contrast, in the antenna holder 2071 according to the first modification of the second embodiment, only the rubber bands 2811 and 2812 of which the extension direction is identical to the extension direction of the belt 74 have a sagging. Thus, in the antenna holder 2071, when the belt 74 is pulled, the rubber bands 283 to 286 of which the extension direction is not identical to the extension direction of the belt 74 extend earlier than the rubber bands 2811 and 2812. After that, the rubber bands 2811 and 2812 extend in the extension direction of the belt 74 after the sagging disappears. Thus, in the antenna holder 2071, since the rubber bands 283 to 286 of which the extension direction is not identical to the extension direction of the belt 74 also extend sufficiently, a force sufficient to attach the polygonal sheet portion 40 closely to the body surface 22 is generated from all rubber bands 2811, 2812, and 283 to 286, and the entire polygonal sheet portion 40 can be reliably closely attached to the body surface 22. In other words, according to the first modification of the second embodiment, all of the first to eighth receiving antennas 41 to 48 of the polygonal sheet portion 40 can be closely attached to the body surface 22 of the subject 2 more reliably.

Second Modification of Second Embodiment

Figure 25:
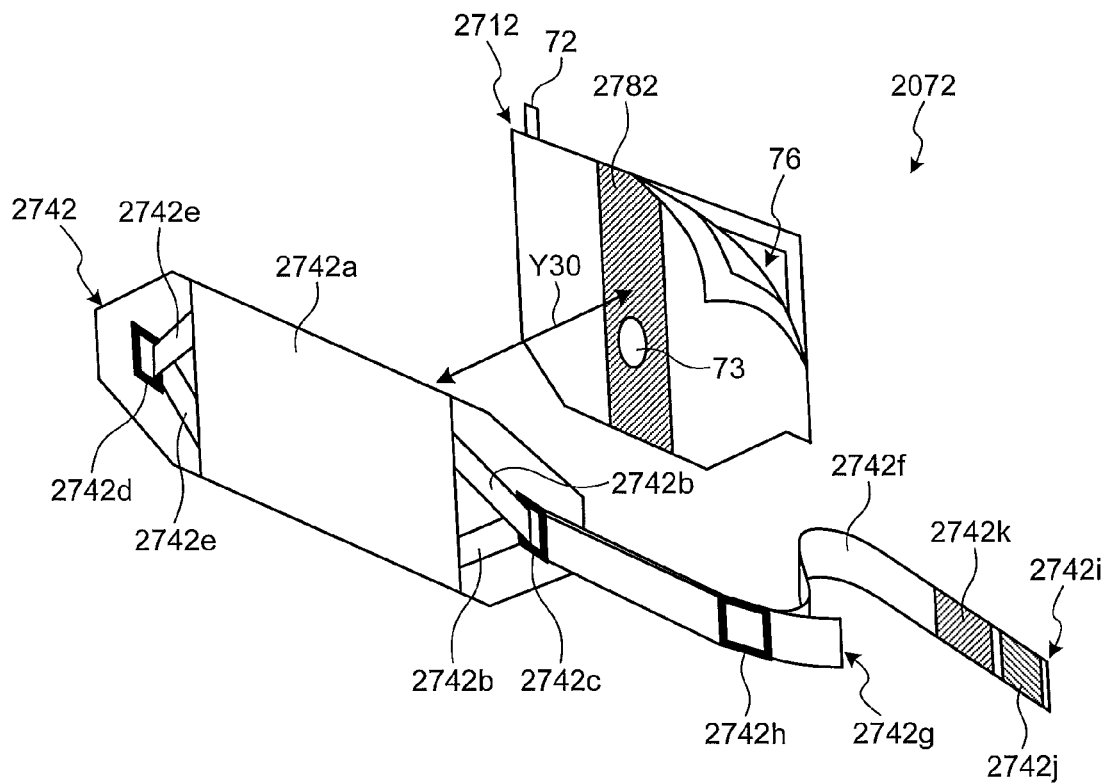
FIG. 25 is a perspective view of an antenna holder according to a second modification of the second embodiment.

Next, a second modification according to the second embodiment will be described. FIG. 25 is a perspective view of an antenna holder according to the second modification of the second embodiment.

As illustrated in FIG. 25, an antenna holder 2072 according to the second modification of the second embodiment includes a container portion 2712 in which the opening 76 is formed and a belt member 2742 that is configured to be detachable from the container portion 2712.

Similarly to the container portion 71, the opening 76 configured to hold the polygonal sheet portion 40 of the acquisition antenna 4 is formed in the container portion 2712. Moreover, a fastener can be open and closed in the same range of areas as the container portion 71, and the positioning hole 73 is formed at the same position as the container portion 71. Further, a hook-and-loop fastener 2782 is formed on a surface of the container portion 2712 that faces the outer side of the subject 2 when the antenna holder 2072 is attached to the subject 2. A loop surface, for example, is formed as the hook-and-loop fastener 2782. The hook-and-loop fastener 2782 is formed in an area that includes the center of the container portion 2712 and extends from the upper end to the lower end of the container portion 2712.

The belt member 2742 includes a body portion 2742a. The body portion 2742a has a larger horizontal width than the horizontal width of the container portion 2712 and a smaller vertical width than the vertical width of the container portion 2712. A hook-and-loop fastener (not illustrated) is formed on a surface of the body portion 2742a that faces the body surface 22 of the subject 2 when the antenna holder 2072 is attached to the subject 2. A hook portion of the hook-and-loop fastener is formed on the body portion 2742a. Due to the hook-and-loop fastener 2782 of the container portion 2712 and the hook-and-loop fastener of the body portion 2742a, the belt member 2742 can be detachably attached to the container portion 2712 as indicated by arrow Y30.

Moreover, both ends of a connecting portion 2742b in a state of being passed through a belt loop 2742c are fixed to the right side of the body portion 2742a. Similarly, both ends of a connecting portion 2742e in a state of being passed through a belt loop 2742d are fixed to the left side of the body portion 2742a. The connecting portions 2742b and 2742e are connected to the body portion 2742a at two points, and the two points are located at positions with a central axis in the longitudinal direction of the belt interposed. Moreover, one end portion 2742g of a belt 2742f is passed through the belt loop 2742c. The end portion 2742g is folded back after being passed through the belt loop 2742c and is passed through a buckle 2742h. A hook portion 2742j and a loop portion 2742k of a hook-and-loop fastener are formed on the other end portion 2742i of the belt 2742f.

In the second modification of the second embodiment, after the polygonal sheet portion 40 of the acquisition antenna 4 is held in the container portion 2712, alignment between the container portion 2712 and the body surface 22 of the subject 2 is performed so that the navel 21 can be seen through the positioning hole 73 of the container portion 2712. After that, the belt member 2742 is fixed to the container portion 2712 using the hook-and-loop fastener so as to correspond to a position that is to be fastened by the belt 2742f. Subsequently, the end portion 2742i of the belt 2742f of the belt member 2742 is passed through the belt loop 2742d on the left side of the body portion 2742a and is folded back, and the hook portion 2742j of the hook-and-loop fastener is pressed and fixed to the loop portion 2742k. In this way, the acquisition antenna 4 is attached to the subject 2 by the belt 2742f. By adjusting a fastening position of the buckle 2742h, it is possible to adjust the length of the belt 2742f.

Figure 26:
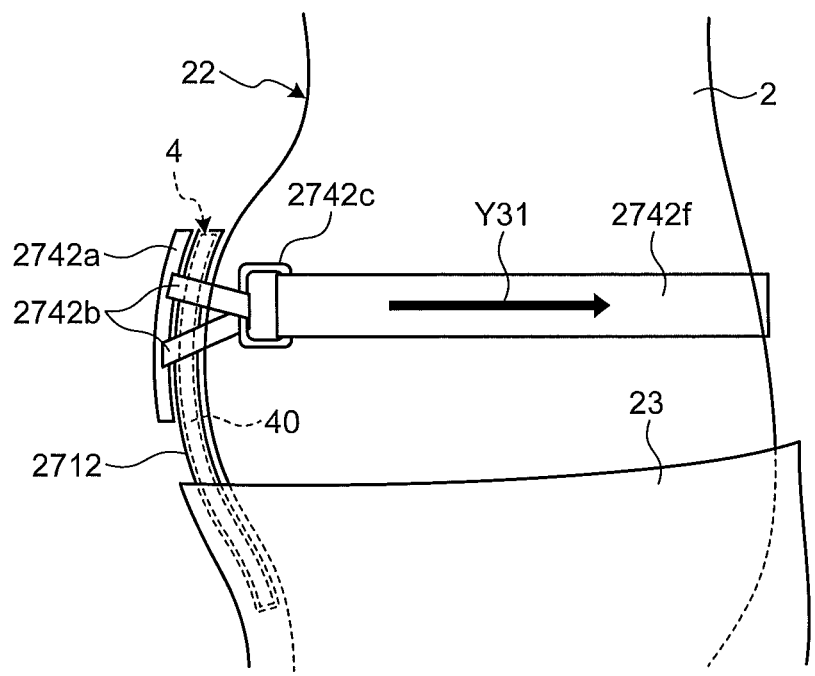
FIG. 26 is a view for describing an attachment state to a subject, of the antenna holder according to the second modification of the second embodiment.

As illustrated in FIG. 26, for example, when the body portion 2742a of the belt member 2742 is attached to the upper portion of the container portion 2712, the upper portion of the polygonal sheet portion 40 of the acquisition antenna 4 can be closely attached to the body surface 22 of the subject 2 according to extension of the belt 2742f in the direction indicated by arrow Y31. Moreover, by holding the lower portion of the container portion 2712 using the clothes of the subject 2 such as pants 23, the entire polygonal sheet portion 40 of the acquisition antenna 4 can be closely attached to the body surface 22 of the subject 2.

According to the second modification of the second embodiment, by allowing the height of the belt 2742f in relation to the polygonal sheet portion 40 to be adjusted, the belt can be united at such a height that the belt is most easily closely attached to the body surface 22 of various subjects 2 of which the individual body measurements are different. Thus, the polygonal sheet portion 40 of the acquisition antenna 4 can be closely attached to the body surface 22.

Moreover, when the present invention is applied to the subject 2 having such a belly shape that the polygonal sheet portion 40 of the acquisition antenna 4 is likely to float from the body surface 22, such as the subject 2 in which a protruding portion of the belly has a small radius, the polygonal sheet portion 40 may be reliably closely attached to the body surface 22 of the subject 2 using at least two belt members 2742.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An antenna apparatus configured to acquire information from a body-insertable apparatus that is configured to be inserted into a subject to move inside the subject, the antenna apparatus comprising:
   an antenna that includes one sheet on which plural receiving antennas are fixed and in which a first positioning hole is formed; and
   an antenna holder that includes a container portion which is configured to hold the antenna at a predetermined position and in a predetermined orientation and in which a second positioning hole is formed at a position corresponding to the first positioning hole when the antenna is held, the antenna holder being configured to be attached to a predetermined position of the subject using the first and second positioning holes as an index when the antenna is held, wherein
   the antenna further includes a cable which extends from the sheet and in which wires connected to the respective receiving antennas are bundled,
   the sheet has an upper side and a bottom side that are parallel to an extension direction of the cable, and
   a base end portion of the cable is disposed at a position that is deviated from an intermediate line of the upper and bottom sides of the sheet and is close to the upper side,
   wherein the container portion of the antenna holder has such a pouch shape that the antenna can be inserted and that has an opening that can be opened and closed,
   wherein the opening is provided from an upper side of the container portion to a position of the cable when the antenna is held in the container portion in such a way that the bottom side of the sheet is positioned at a bottom of the container portion,
   wherein the base end portion of the cable is positioned at an end portion of the opening and the first positioning hole is aligned with the second positioning hole when the antenna is held in the container portion in such a way that the bottom side of the sheet is positioned at the bottom of the container portion, and
   wherein the base end portion of the cable is caught at the end portion of the opening and the first positioning hole is not aligned with the second positioning hole when the antenna is held in the container portion in such a way that the upper side of the sheet is oriented to the bottom of the container portion.

2. The antenna apparatus according to claim 1, wherein the antenna holder includes:
   a belt that is attached to the container portion to fix the container portion to the subject; and
   a rubber band that is formed on an outer surface of the container portion and is stretchable in a direction crossing an extension direction of the belt.

3. The antenna apparatus according to claim 2, wherein the belt is detachable from the container portion.

4. The antenna apparatus according to claim 1, wherein the sheet is octagonal.

5. A body-insertable apparatus system that is inserted into a subject to acquire internal information of the subject, the body-insertable apparatus system comprising:
   a body-insertable apparatus configured to be inserted into the subject to acquire an in-vivo image of the subject and wirelessly transmit image data to the outside while moving inside the subject;
   an antenna that includes one sheet on which plural receiving antennas that receive the image data transmitted wirelessly from the body-insertable apparatus are fixed and in which a first positioning hole is formed;
   an antenna holder that includes a container portion which is configured to hold the antenna at a predetermined position and in a predetermined orientation and in which a second positioning hole is formed at a position corresponding to the first positioning hole when the antenna is held, the antenna holder being configured to be attached to a predetermined position of the subject using the first and second positioning holes as an index when the antenna is held;

a receiving device that stores the image data received by the antenna and received signal strengths of the plural receiving antennas when the image data is received; and an information processing device to which the image data stored in the receiving device is transmitted and which displays the in-vivo image of the subject on a display unit, wherein the antenna further includes a cable which extends from the sheet and in which wires connected to the respective receiving antennas are bundled, the sheet has an upper side and a bottom side that are parallel to an extension direction of the cable, and a base end portion of the cable is disposed at a position that is deviated from an intermediate line of the upper and bottom sides of the sheet and is close to the upper side, and the information processing device includes a position information estimating unit configured to estimate position information of the body-insertable apparatus when the image data is received, based on the respective received signal strengths of the plural receiving antennas included in the image data, wherein the container portion of the antenna holder has such a pouch shape that the antenna can be inserted and that has an opening that can be opened and closed, wherein the opening is provided from an upper side of the container portion to a position of the cable when the antenna is held in the container portion in such a way that the bottom side of the sheet is positioned at a bottom of the container portion, wherein the base end portion of the cable is positioned at an end portion of the opening and the first positioning hole is aligned with the second positioning hole when the antenna is held in the container portion in such a way that the bottom side of the sheet is positioned at the bottom of the container portion, and wherein the base end portion of the cable is caught at the end portion of the opening and the first positioning hole is not aligned with the second positioning hole when the antenna is held in the container portion in such a way that the upper side of the sheet is oriented to the bottom of the container portion.

\* \* \* \* \*